(12) United States Patent
Faris et al.

(10) Patent No.: US 8,481,303 B2
(45) Date of Patent: Jul. 9, 2013

(54) MICROFLUIDIC DEVICE FOR CELL CULTURE

(75) Inventors: Ronald A. Faris, Elmira, NY (US); Vasiliy N. Goral, Painted Post, NY (US); Miya (Yi-Cheng) Hsieh, Yi-Lan (TW); Odessa N. Petzold, Elmira, NY (US); Po Ki Yuen, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 494 days.

(21) Appl. No.: 12/716,680

(22) Filed: Mar. 3, 2010

(65) Prior Publication Data

US 2011/0086427 A1 Apr. 14, 2011

Related U.S. Application Data

(60) Provisional application No. 61/250,754, filed on Oct. 12, 2009.

(51) Int. Cl.
*C12M 3/00* (2006.01)
(52) U.S. Cl.
USPC .................................. 435/289.1; 435/299.1
(58) Field of Classification Search
None
See application file for complete search history.

(56) References Cited

U.S. PATENT DOCUMENTS

| 4,454,721 | A | 6/1984 | Hürlimann et al. ............. 60/659 |
| 5,792,653 | A | 8/1998 | Weibezahn et al. ......... 435/288.5 |
| 6,030,829 | A | 2/2000 | Dannoux et al. ............ 435/288.3 |
| 6,197,575 | B1 | 3/2001 | Griffith et al. |
| 6,306,644 | B1 | 10/2001 | Marx et al. .................. 435/294.1 |
| 6,306,646 | B1 | 10/2001 | Saad et al. ................... 435/305.1 |
| 6,653,124 | B1 | 11/2003 | Freeman et al. |
| 6,720,469 | B1 | 4/2004 | Curtis et al. .................... 602/41 |
| 7,018,418 | B2 | 3/2006 | Amrich et al. ................ 623/23.5 |
| 7,033,821 | B2 | 4/2006 | Kim et al. ................... 435/288.4 |
| 7,190,449 | B2 | 3/2007 | O'Connell .................... 356/246 |
| 7,329,537 | B2 | 2/2008 | Qiu ............................. 435/288.3 |
| 7,470,424 | B2 | 12/2008 | Kataoka et al. ............... 424/93.1 |
| 7,569,354 | B2 | 8/2009 | Okano et al. .................... 435/7.1 |
| 2001/0024805 | A1 | 9/2001 | Williams et al. ................ 435/29 |
| 2003/0030184 | A1 | 2/2003 | Kim et al. ...................... 264/325 |
| 2003/0082795 | A1 | 5/2003 | Shuler et al. ................ 435/286.1 |
| 2004/0067585 | A1 | 4/2004 | Wang et al. ................... 435/395 |
| 2004/0125266 | A1 | 7/2004 | Miyauchi et al. ............... 349/57 |
| 2004/0259177 | A1 | 12/2004 | Lowery et al. ............... 435/7.23 |
| 2005/0095699 | A1 | 5/2005 | Miyauchi et al. .......... 435/299.1 |
| 2005/0106728 | A1 | 5/2005 | Burgess et al. ............... 435/440 |
| 2006/0097361 | A1 | 5/2006 | Tanaka et al. ................. 257/643 |
| 2006/0228386 | A1 | 10/2006 | Stephens et al. .............. 424/401 |
| 2007/0059565 | A1 | 3/2007 | Siu .................................. 429/2 |
| 2007/0059763 | A1 | 3/2007 | Okano et al. .................... 435/7.1 |
| 2007/0249044 | A1 | 10/2007 | Desai et al. ................... 435/325 |
| 2008/0018024 | A1 | 1/2008 | Kataho et al. ................. 264/485 |
| 2008/0057578 | A1 | 3/2008 | Kuwabara ..................... 435/366 |
| 2008/0233607 | A1 | 9/2008 | Yu et al. ......................... 435/29 |
| 2009/0042200 | A1 | 2/2009 | Okano et al. ...................... 435/6 |
| 2009/0042739 | A1 | 2/2009 | Okano et al. .................... 506/12 |

FOREIGN PATENT DOCUMENTS

| EP | 0 862 540 | 7/2000 |
| GB | 1 437 404 | 5/1976 |
| GB | 2 427 688 | 1/2007 |
| JP | 2000-231007 | 8/2000 |
| WO | WO 95/12369 | 5/1995 |
| WO | WO 97/19027 | 5/1997 |
| WO | WO 99/45860 | 9/1999 |
| WO | WO 03/101618 | 12/2003 |
| WO | 2006/052223 | 5/2006 |
| WO | WO 2006/114098 | 11/2006 |

OTHER PUBLICATIONS

Levitan, I., "A Chamber to Permit Invasive Manipulation of Adherent Cells in Laminar Flow tih Minimal Disturbance of the Flow Field", Annals of Biomedical Engineering, vol. 28. No. 10, Oct. 1, 2000 pp. 1184-1193.

Takayama S, "Patterning of cells and their environments using multiple laminar fluid flows in capillary networks." Proceedings of the National Academey of Sciences of USA, vol. 96, May 1, 1999 pp. 5545-5548.

Brown, D. "Improvements to parallel plate flow chambers to reduce reagent and cellular requirements", BMC Immunology, vol. 2, No. 1, Sep. 11, 2001, p. 9.

Toy Y-C, "A configurable three-dimensional microenvironment in a hepatocytes culture", Assay and Drug Development Technologies, vol. 3, No. 2, Jan. 1, 2005, pp. 169-176.

Park, T H., "Integration of cell culture and microfabrication technology", Biotechnology Progress, vol. 19, No. 2, Jan. 1, 2003, pp. 243-253.

A. Abbott, "Biology's new dimension",*Nature*, Aug. 2003, vol. 424, pp. 870-872.

C.J. Bettinger, et al., "Microfabrication of poly(glycerol-sebacate) for contact guidance applications", *Biomaterials*, 2006, vol. 27, pp. 2558-2565.

(Continued)

*Primary Examiner* — Jim Ketter

(74) *Attorney, Agent, or Firm* — Susan S. Wilks

(57) ABSTRACT

A microfluidic cell culture apparatus includes a cell retention chamber and a perfusion channel. The cell retention chamber has a structured surface. The structured surface includes a major surface from which a plurality of projections extends into the chamber. The plurality of projections are arranged to suspend cells cultured in the chamber above the major surface. The first perfusion channel is configured to provide laminar flow of a fluid through the channel and forms a plurality of openings in communication with the cell retention chamber. The openings are configured to prevent cells from the retention chamber from entering the perfusion channel.

20 Claims, 25 Drawing Sheets

OTHER PUBLICATIONS

J.L. Charest, et al., "Myoblast alignment and differentiation on cell culture substrates with microscale topography and model chemistries", *Biomaterials*, 2007, vol. 28, pp. 2202-2210.

C.H. Choi, et al., "Cell interaction with three-dimensional sharp-tip nanotopography", *Biomaterials*, 2007, vol. 28, pp. 1672-1679.

C.H. Choi, et al., "Fabrication of a dense array of tall nanostructures over a large sample area with sidewall profile and tip sharpness control", *Nanotechnology*, 2006, vol. 17, pp. 5326-5333.

H.G. Craighead, et al., "Chemical and topographical patterning for directed cell attachment", *Current Opinion in Solid State and Materials Science*, 2001, vol. 5, pp. 177-184.

E. Cukierman, et al., "Taking Cell-Matrix Adhesions to the Third Dimension",*Science*, Nov. 23, 2001, vol. 294, pp. 1708-1712.

A. Curtis, et al., "Topographical control of cells",*Biomaterials*, 1997, vol. 18, pp. 1573-1583.

M.J. Dalby, et al., "Polymer-Demixed Nanotopography: Control of Fibroblast Spreading and Proliferation", *Tissue Engineering*, 2002, vol. 8, No. 6, pp. 1099-1108.

M.R. Dusseiller, et al., "An inverted microcontact printing method on topographically structured polystyrene chips for arrayed micro-3-D culturing of single cells",*Biomaterials*, 2005, vol. 26, pp. 5917-5925.

M.R. Dusseiller, et al., "Microfabricated three-dimensional environments for single cell studies", *Biointerphases*, Mar. 2006, vol. 1, No. 1, pp. 1-4.

R.G. Flemming, et al., "Effects of synthetic micro- and nano-structured surfaces on cell behavior", *Biomaterials*, 1999, vol. 20, pp. 573-588.

A. Folch, et al., "Microfabricated elastomeric stencils for micropatterning cell cultures", *Journal of Biomedical Materials Research*, 2000, vol. 52, No. 2, pp. 346-353.

J. Fukuda, et al., "Micromolding of photocrosslinkable chitosan hydrogel for spheroid microarray and co-cultures", *Biomaterials*, 2006, vol. 27, pp. 5259-5267.

J. Fukuda, et al., "Novel hepatocyte culture system developed using microfabrication and collagen/polyethylene glycol microcontact printing", *Biomaterials*, 2006, vol. 27, pp. 1061-1070.

J. Fukuda, et al., "Orderly Arrangement of Hepatocyte Spheroids on a Microfabricated Chip", *Tissue Engineering*, 2005, vol. 11, No. 7/8, pp. 1254-1262.

N. Gadegaard, et al, "Applications of nano-patterning to tissue engineering", *Microelectronic Engineering*, 2006, vol. 83, pp. 1577-1581.

S. Giselbrecht, et al., "3D tissue culture substrates produced by microthermoforming of pre-processed polymer films", *Biomedical Microdevices*, 2006, vol. 8, No. 3, pp. 191-199.

S. Giselbrecht, et al., "Microthermoforming as a novel technique for manufacturing scaffolds in tissue engineering (CellChips®)", *IEE Proceedings-Nanobiotechnology*, Aug. 2004, vol. 151, No. 4, pp. 151-157.

E. Gottwald, et al., "A chip-based platform for the in vitro generation of tissues in three-dimensional organization", *Lab on a Chip*, 2007, vol. 7, pp. 777-785.

D.W. Hamilton, et al., "The effect of substratum topography on osteoblast adhesion mediated signal transduction and phosphorylation", *Biomaterials*, 2007, vol. 28, pp. 1806-1819.

X. Jiang, et al., "Controlling Mammalian Cell Spreading and Cytoskeletal Arrangement with Conveniently Fabricated Continuous Wavy Features on Poly(dimethylsiloxane)",*Langmuir*, 2002, vol. 18, pp. 3273-3280.

F. Johansson, et al., "Axonal outgrowth on nano-imprinted patterns", *Biomaterials*, 2006, vol. 27, pp. 1251-1258.

J.M. Karp, et al., "Controlling size, shape and homogeneity of embryoid bodies using poly(ethylene glycol) microwells", *Lab on a Chip*, 2007, vol. 7, pp. 786-794.

A. Khademhosseini, et al., "Co-culture of human embryonic stem cells with murine embryonic fibroblasts on microwell-patterned substrates", *Biomaterials*, 2006, vol. 27, pp. 5968-5977.

A. Khademhosseini, et al., "Microscale technologies for tissue engineering and biology", *Proceedings of the National Academy of Sciences of the United States of America*, 2006, vol. 103, No. 8, pp. 2480-2487.

A. Khademhosseini, et al., "Molded polyethylene glycol microstructures for capturing cells within microfluidic channels", *Lab on a Chip*, 2004, vol. 4, No. 5, pp. 425-430.

S. Kidambi, et al., "Patterned Co-Culture of Primary Hepatocytes and Fibroblasts Using Polyelectrolyte Multilayer Templates," *Macromolecular Bioscience*, 2007, vol. 7, pp. 344-353.

D.H. Kim, et al., "Guided Three-Dimensional Growth of Functional Cardiomyocytes on Polyethylene Glycol Nanostructures", *Langmuir*, 2006, vol. 22, pp. 5419-5426.

H. Kim, et al., "Live Lymphocyte Arrays for Biosensing**",*Advanced Functional Materials*, 2006, vol. 16, pp. 1313-1323.

J.B. Kim, et al., "Three-dimensional in vitro tissue culture models of breast cancer—a review", *Breast Cancer Research and Treatment*, 2004, vol. 85, pp. 281-291.

J.B. Kim, et al., "Three-dimensional tissue culture models in cancer biology",*Seminars in Cancer Biology*, 2005, vol. 15, pp. 365-377.

J.N. Kuo, et al., "An SU-8 microlens array fabricated by soft replica molding for cell counting applications", *Journal of Micromechanics and Microengineering*, 2007, vol. 17, No. 4, pp. 693-699.

J.C. Mohr, et al., "3-D microwell culture of human embryonic stem cells",*Biomaterials*, 2006, vol. 27, pp. 6032-6042.

D. Motlagh, et al., "Microtextured substrata alter gene expression, protein localization and the shape of cardiac myocytes", *Biomaterials*, 2003, vol. 24, pp. 2463-2476.

S. Nomura, et al., "Cell Culture on Nanopillar Sheet: Study of HeLa Cells on Nanφillar Sheet", *Japanese Journal of Applied Physics*, 2005, vol. 44, No. 37, pp. L1184-L1186.

A. Nur-E-Kamal, et al., "Three dimensional nanofibrillar surfaces induce activation of Rac", *Biochemical and Biophysical Research Communications*, 2005, vol. 331, pp. 428-434.

A. Nur-E-Kamal, et al., "Three-Dimensional Nanofibrillar Surfaces Promote Self-Renewal in Mouse Embryonic Stem Cells", *Stem Cells*, 2006, vol. 24, pp. 426-433.

B.J. Papenburg, et al., "One-step fabrication of porous micropatterned scaffolds to control cell behavior", *Biomaterials*, 2007, vol. 28, pp. 1998-2009.

N. Patrito, et al., "Spatially Controlled Cell Adhesion via Micropatterned Surface Modification of Poly(dimethylsiloxane)", *Langmuir*, 2007, vol. 23, pp. 715-719.

S. Petronis, et al., "Model porous surfaces for systematic studies of material-cell interactions", *Journal of Biomedical Materials Research Part A*, 2006, vol. 66A, No. 3, pp. 707-721.

J.R. Rettig, et al., "Large-Scale Single-Cell Trapping and Imaging Using Microwell Arrays",*Anal. Chem.*, 2005, vol. 77, pp. 5628-5634.

S. Sarkar, et al., "Development and characterization of a porous micro-patterned scaffold for vascular tissue engineering applications", *Biomaterials*, 2006, vol. 27, pp. 4775-4782.

H. Shin, "Fabrication methods of an engineered microenvironment for analysis of cell-biomaterial interactions", *Biomaterials*, 2007, vol. 28, pp. 126-133.

T.R. Sodunke, et al., "Micropatterns of Matrigel for three-dimensional epithelial cultures",*Biomaterials*, 2007, vol. 28, pp. 4006-4016.

W.T. Su, et al., "Control Cell Behavior on Physical Topographical Surface", *Japanese Journal of Applied Physics*, 2004, vol. 43, No. 6B, pp. 3806-3809.

Y.C. Toh, et al., "A novel 3D mammalian cell perfusion-culture system in microfluidic channels", Lab on a Chip, 2007, vol. 7, pp. 302-309.

M. Tanaka, et al., "Control of hepatocyte adhesion and function on self-organized honeycomb-patterned polymer film", *Colloids and Surfaces A: Physicochem. Eng. Aspects*, 2006, vol. 284-285, pp. 464-469.

Y. Torisawa, et al., "A multicellular spheroid array to realize spheroid formation, culture, and viability assay on a chip", *Biomaterials*, 2007, vol. 28, pp. 559-566.

Y. Torisawa, et al., "Three-dimensional micro-culture system with a silicon-based cell array device for multi-channel drug sensitivity test", *Sensors and Actuators B*, 2005, vol. 108, pp. 654-659.

I.Y. Tsai, et al., "Novel transparent nano- to micro-heterogeneous substrates for in-situ cell migration study", *Journal of Biomedical Materials Research Part A*, 2007, vol. 80A, No. 2, pp. 509-512.

A.M.P. Turner, et al., "Attachment of astroglial cells to microfabricated pillar arrays of different geometries", *Journal of Biomedical Materials Research*, 2000, vol. 51, No. 3, pp. 430-441.

V.M. Weaver, et al., "Reversion of the Malignant Phenotype of Human Breast Cells in Three-Dimensional Culture and In Vivo by Integrin Blocking Antibodies", *The Journal of Cell Biology*, 1997, vol. 137, No. 1, pp. 231-245.

Z.Z. Wu, et al., "Interfacing SH-SY5Y human neuroblastoma cells with SU-8 microstructures", *Colloids and Surfaces B: Biointerfaces*, 2006, vol. 52, pp. 14-21.

E.K.F. Yim, et al., "Significance of synthetic nanostructures in dictating cellular response", *Nanomedicine : Nanotechnology, Biology, and Medicine*, 2005, vol. 1, pp. 10-21.

C. Zhijiang, "Biocompatibility and Biodegradation of novel PHB porous substrates with controlled multipore size by emulsion templates method", *J. Mater. Sci: Mater. Med.*, 2006, vol. 17, pp. 1297-1303.

MICROFLUIDIC DEVICE FOR CELL CULTURE

CLAIMING BENEFIT OF PRIOR FILED U.S. APPLICATION

This application claims the benefit of U.S. Provisional Application Ser. No. 61/250,754, filed on Oct. 12, 2009. The content of this document and the entire disclosure of publications, patents, and patent documents mentioned herein are incorporated by reference.

FIELD

The present disclosure relates to apparatus for culturing cells; more particularly to microfluidic cell culture apparatuses.

BACKGROUND

Cells cultured on flat cell culture ware often provide artificial two-dimensional sheets of cells that may have significantly different morphology and function from their in vivo counterparts. Cultured cells are important to modern drug discovery and development and are widely used for drug testing. However, if results from such testing are not indicative of responses from cells in vivo, the relevance of the results may be diminished. Cells in the human body experience three dimensional environments completely surrounded by other cells, membranes, fibrous layers, adhesion proteins, etc. Thus, cell culture apparatuses that better mimic in vivo conditions and that prompt cultured cells to have in vivo-like morphology and function are desirable.

Much progress has been made in cell culture configuration and systems to better mimic in vivo conditions and maintain differentiated cells, such as hepatocytes, in culture for longer periods of time. For example, collagen sandwich culture systems, 3D cell culture, and microfluidic perfusion systems have provided some enhancement in cell performance relative to conventional cultures devices in maintaining viable cell cultures with some phenotypic relevance. Other methodologies that have been used to prolong cell viability and function include the use of modified cell culture media, co-cultures, and the use of various extracellular matrices to promote 3D cellular organization. However, mimicking complex in vivo microenvironment that modulates cellular function for successful long-term cultures of cells remains a challenge. Accordingly, even with such advances, limited improvement in cell cultured cell function has been achieved.

BRIEF SUMMARY

The present disclosure describes, among other things, microfluidic devices that provide dynamic cell culture conditions via multiple perfusion channels and virtual suspension of cells on structured supports or encapsulated by structured supports. The devices may mimic the architecture, perfusion and flow of tissue in vivo and allow for formation of tissue-like structure and morphology. For example, in the Examples provided below, hepatocytes cultured on devices described herein showed restored membrane polarity that was extended in three dimensions, formation of bile canaliculi structures, and transport function without the addition of biological or synthetic matrices or coagulants.

The devices described herein have a perfusion channel through which cell culture medium or other fluid compositions may be flowed. The perfusion channel is in fluid communication with a cell retention chamber in which cells may be cultured. The cell retention chamber includes a structured surfaces configured to prevent cell spreading, which may promote three-dimensional cell morphology. The structured surfaces include projections configured to suspend cells above the bottom of the structured surface. The surface area of the surface of the projections with which the cells come into contact, in many embodiments, is less than the contact surface area of a cell to be cultured in the device (i.e., less than the surface area of a cell that would come into contact with a flat, non-structured surface). By limiting the surface area that the cells may contact, cell spreading may be inhibited and three-dimensional cell morphology may be promoted. In some instances, the structured surface can promote or retain cell polarity, such as polarity of hepatocytes.

The structured surfaces may form one or more troughs through which fluid may flow. The bottom of the troughs may be formed by the bottom of the structured surface and the sides of the projections may form the sides of the trough. In various embodiments, the microfluidic culture devices have an inlet and outlet in fluid communication with one or more troughs of the structured surfaces that allow fluid to be introduced into or removed from the troughs. In situations where the cultured cells form tight cell-cell junctions (e.g., adopt tissue like morphology), the cells may fluidly isolate the troughs and the perfusion channel, allowing independent gradients to be formed across the cell chamber. In addition, the trough(s) and perfusion channel can be effectively used to simulate multidirectional flow in vivo. In some cases, the carious gradients that may result or the multidirectional flow may encourage cell polarity.

The devices and methods described herein may provide one or more advantages over prior microfluidic or other culture devices. For example, embodiments of the devices described herein may provide structural design to enable 3D tissue-like organization of cells and restoration of in vivo-like membrane polarity, may provide sustainable dynamic in vivo-like conditions for long-term cell culture and cell-specific functionality in vitro for evaluation of toxicity (including chronic toxicity) and studies of drug-drug interaction (over longer term), may provide dynamic cell culture conditions, such as controlled supply of oxygen and nutrients, oxygen gradient and shear stress control, and may allow for control of oxygen levels and nutrients to mimic physiological conditions. The multiple flow channels provide efficient and effective transport of nutrients, removal of waste, and supply of oxygen. The troughs and perfusion channel can be effectively used independently to generate gradients across the cell chamber and simulate multidirectional flow in vivo. A perfusion regime that promotes the restoration of polarity and extends a bile canalicular structure in three dimensions can be realized. These and other advantages of the various embodiments of the devices and methods described herein will be readily apparent to those of skill in the art upon reading the disclosure presented herein.

BRIEF DESCRIPTION OF THE DRAWINGS

In FIG. 22A, the left most panel is a fluorescent image (5×) and the three rightmost panels are brightfield images at 5×, 20× and 20× (left to right, respectively). In FIG. 22B, the left most panel is a fluorescent image (10×), the middle panel is a brightfield image (10×), and the right panel is a brightfield image (20×).

Figure 1:
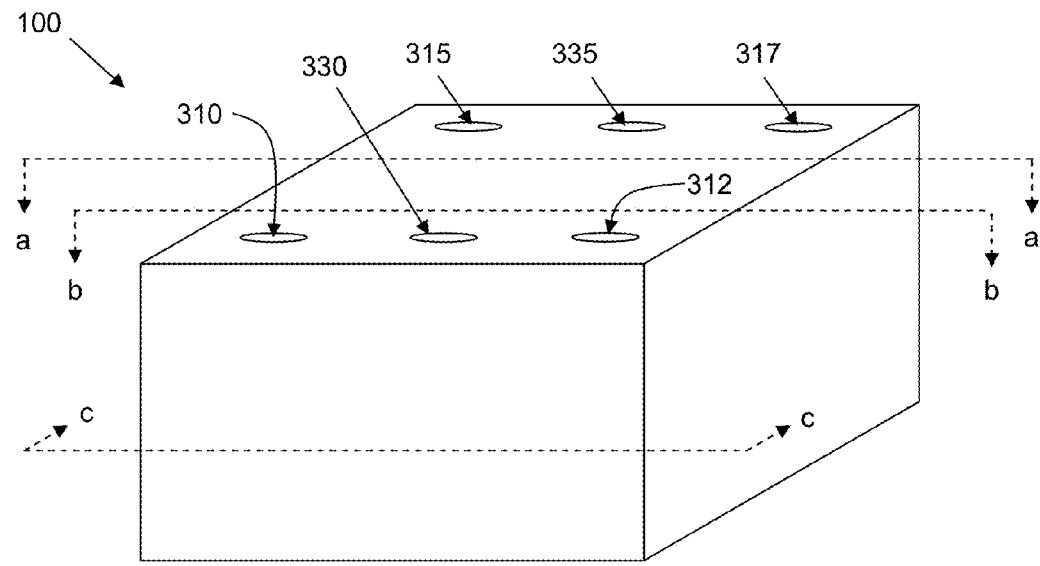
FIG. 1 is a schematic perspective view of an embodiment of a microfluidic apparatus.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

Any direction referred to herein, such as "top," "bottom," "left," "right," "upper," "lower," "above," "below," and other directions and orientations are described herein for clarity in reference to the figures and are not to be limiting of an actual device or system or use of the device or system. Devices or systems as described herein may be used in a number of directions and orientations.

As used herein, "structured surface" means a surface having a predetermined topography. A structured surface includes a major surface and projections extending from the major surface, which define the predetermined topography. The projections have a surface facing in a direction substantially the same as the major surface, and these surfaces of the projections, along with the exposed portions of the major surface (those portions on which no projection lies), comprise the "structured surface".

As used herein, a "trough", as it relates to a structured surface, means a depression or channel formed along the major surface of the structured surface between at least two projections extending from the major surface. In many embodiments, a "trough" is a continuous path that extends along the length of the major surface of the structured surface. A trough may take any path along the major surface and is defined, at least in part, by the projections extending from the major surface.

As used herein, "suspend", as it related to cells relative to a surface, means "to support the cell above the surface."

As used herein, a "perfusion channel", as it relates to a microfluidic device for culturing cells, means a channel through which a cell culture medium may flow, which channel is configured to allow the cell culture medium to perfuse cells cultured in the device. Typically, a perfusion channel is configured to provide laminar flow (i.e., non-turbulent flow) of the cell culture medium and forms openings through which the cell culture medium may pass to perfuse the cells.

The present disclosure describes, among other things, microfluidic devices that provide dynamic cell culture conditions via multiple perfusion channels and virtual suspension of cells on structured supports or encapsulated by structured supports. The devices may mimic the architecture, perfusion and flow of tissue in vivo, allowing for cultured cells to adopt in vivo-like morphology and functionality. Such devices, as described herein below, have been shown to promote and maintain 3D in vivo-like cellular structure that promotes cell-cell signaling, the restoration of polarity in three dimensions, and cell-specific functionality in vitro for long term cell culture without addition of biological or synthetic matrices or coagulants.

In various embodiments, such devices have multiple inlets and outlets for independent flow as well as for seeding or infusing cells into a ready-to-use (no assembly required) device. The devices may allow for control of perfusion to provide optimized physiologically relevant cell culture conditions, such as media flow and shear stress similar to tissue microcirculation, oxygen and growth media supply, and removal of waste components, catabolites and metabolites. The devices may also have multiple perfusion channels where there are two parallel flow channels on either side of the cell chamber and there is a lower flow channel that supports independent flow and virtual suspension of cells on structured supports (pillars or channel sub-structures) at the bottom of the cell chamber. Such devices may be used for testing drug candidates on target cells, drug-drug interactions, metabolism and toxicity of new drug candidates as well as their metabolites, and transport of drug candidates and their metabolites. The devices may be arrayed and packaged in format for throughput to perform screening assays, such as toxicity screening. In various embodiments, the devices are configured to be fitted (or are fitted) with biosensors to monitor environmental conditions such as $O_2$, $CO_2$, flow rates, pH and temperature.

Referring now to FIG. 1, a schematic perspective view of an embodiment of microfluidic cell culture apparatus 100 is shown. The depicted apparatus 100 has an inlet 330 and an outlet 335 in communication with an internal cell retention chamber (not show in FIG. 1). The depicted apparatus also has an inlet 310 and an outlet 315 in fluid communication with a first internal perfusion channel (not show in FIG. 1) and an inlet 312 and an outlet 317 in fluid communication with a second internal perfusion channel (not show in FIG. 1). It will be understood that a cell culture apparatus 100 as described herein may include any number of inlets 310, 312 and outlets 315, 317 and any number of perfusion channels. It will be further understood that an inlet 310, 312, as depicted, may be an outlet, and an outlet 315, 317, as depicted, may be an inlet, depending on the direction of fluid flow. One inlet or one outlet is in fluid communication with more than one perfusion channel.

Figure 2A:
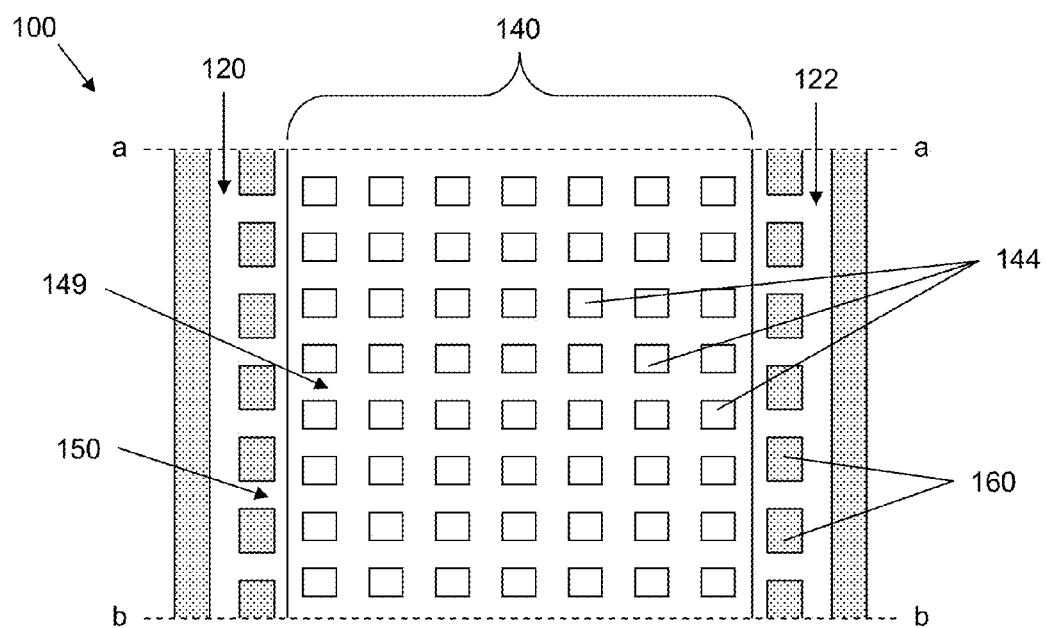
FIGS. 2A-C are schematic cross sections of embodiments of a microfluidic device of FIG. 1, taken through line c-c between lines a-a and b-b of FIG. 1.
Figure 2B:
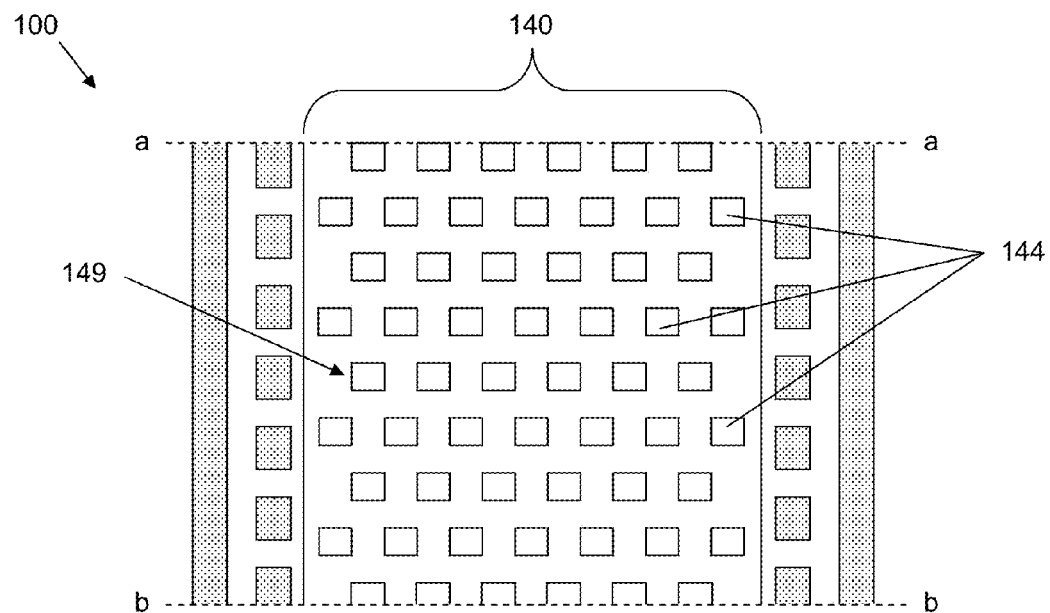
Figure 2C:
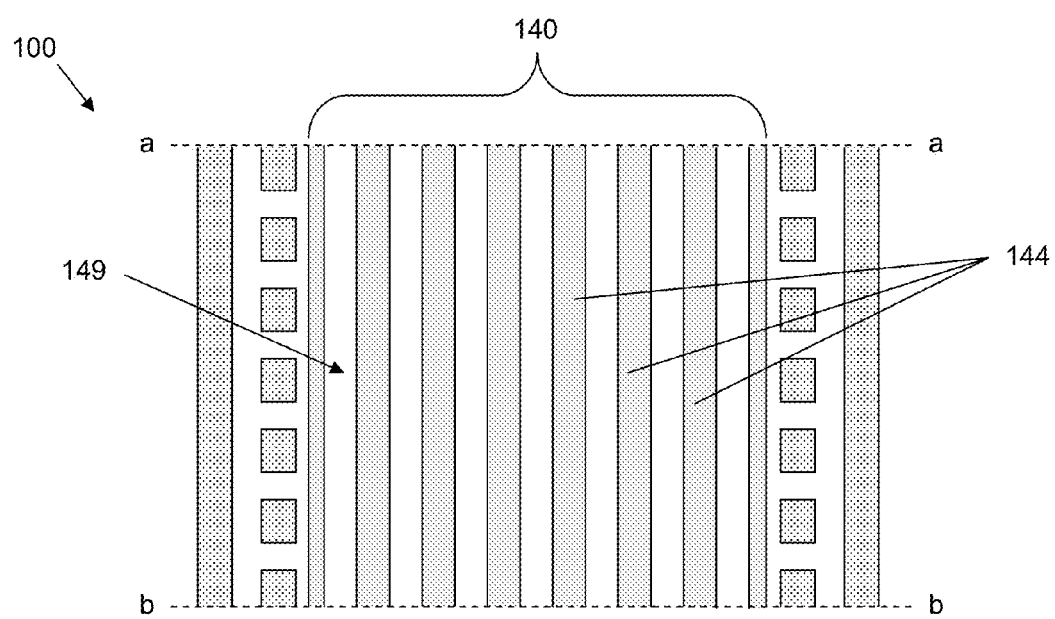

Referring now to FIGS. 2A-C, schematic cross sections of various embodiments of the apparatus 100 of FIG. 1, taken along line c-c between lines a-a and b-b as shown in FIG. 1, are shown. The cell retention chamber of the apparatus 100 includes a structured surface 140 on which cells may be cultured. The structure surface 140 includes a major surface 149 (bottom surface in the depicted figures) facing the cell retention chamber. A plurality of projections 144 extend from the major surface 149 into the cell retention chamber. As illustrated in the depicted embodiments, the projections 144 may be arranged in any suitable manner and may be of any suitable shape or configuration. In the embodiments depicted in FIGS. 2A-2B, the projections 144 are in the form of pillars. While the pillars shown in FIGS. 2A-B are shown as having a rectangular cross-sectional shape, it will be understood that the pillars may have any suitable cross-sectional shape, such as circular, ellipsoid, hexagonal, triangular, v-shaped, or irregular-shaped, or the like). In the embodiment shown in FIG. 2C, the projections 144 form ridges extending the length of the structured surface 140. While the ridges depicted in FIG. 2C are linear, it will be understood that the ridges be of any suitable shape including sinusoidal, serpentine, irregular, or the like.

Figure 3A:
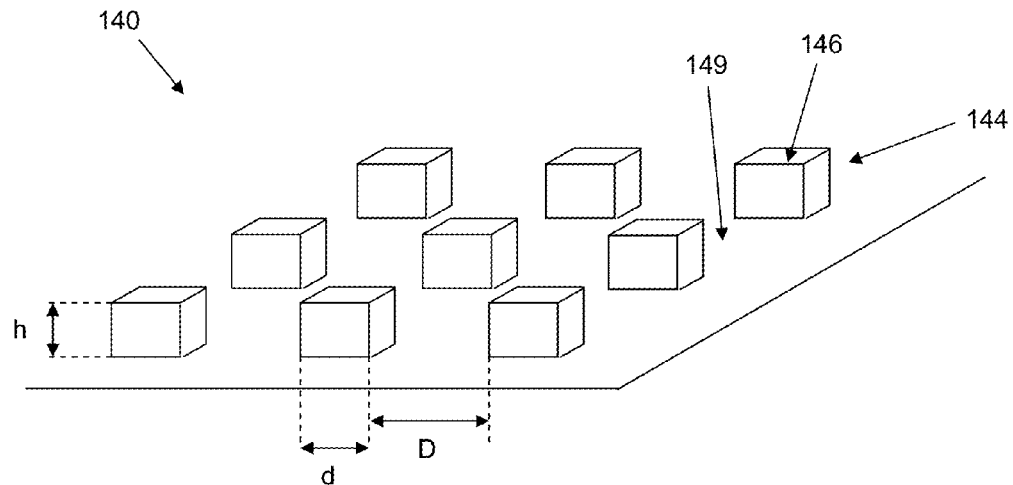
FIGS. 3A-B are schematic diagrams of structured surfaces without (A) and with (B) cells disposed on the surface.
Figure 3B:
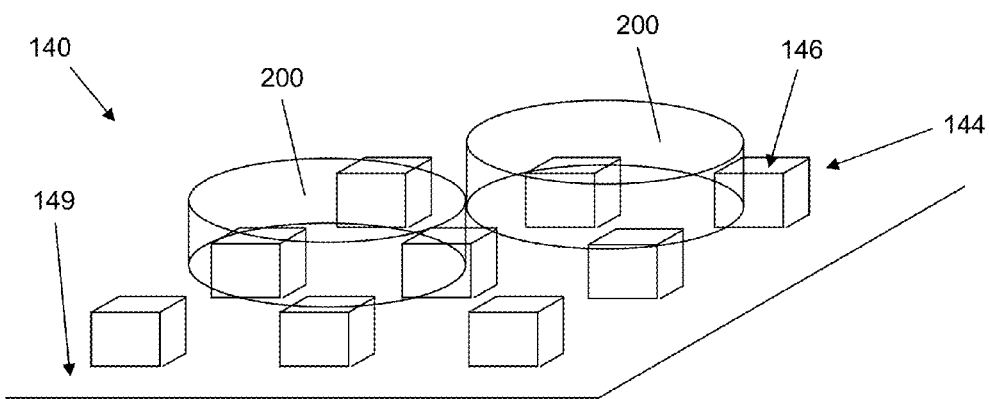

Referring now to FIGS. 3A-C, schematic views of a structured surface 140 of a cell retention chamber, without (3A) and with (3B) cells 200 cultured on the surface 140 are shown. The structured surface 140 is configured to restrict spreading of cells 200 cultured on the surface. This can be accomplished by minimizing the surface area of the structured surface 140 that contacts the cells when the cells 200 are cultured in the cell retention chamber of the apparatus. In general, the projections 144 have a diametric dimension d, such as a width, diameter, or the like, that is less than a diametric dimension of a cell to be cultured in the chamber. For example, the diametric dimension d of a cell contacting surface 146 (the top surface in the depicted embodiment, which is generally opposing the surface in contact with or extending from the major surface 149) of a projection 144 may be about half the diametric dimension of cells 200 to be cultured in the apparatus. In various embodiments, the diametric dimension d of the cell contacting surface 146 of the projection 144 is between about 5 micrometers and about 15 micrometers or between about 5 micrometers and 10 micrometers. When projections 144 are pillars (as opposed to elongate ridges as shown in FIG. 2C), the surface area of the cell contacting surface 146 may be less than the surface area of a cell that would come into contact with a flat, non-structured surface. For example, the surface area of the cell contacting surface 146 may be one half, one quarter, or less than on quarter of the surface are of a cell that would come into contact with a flat, non-structured surface. In various embodiments, the surface area of the cell contacting surface 146 is between about 25 square micrometers and 225 square micrometers.

Further, the projections 144 are spaced apart such that the distance D between neighboring projections 144 is sufficiently small to prevent a cell from contacting the major surface 149 of the structured surface. In this manner, the projections 144 suspend the cells 200 above the major surface 149, and the surface area of the structured surface 140 that the cells 200 may come into contact with is limited to the cell contacting surfaces 146 of the projections 144. The distance D between neighboring projections 144 may be any suitable distance, such as less than the diametric dimension of an average cell 200 to be cultured in the apparatus or less than half the diametric dimension of an average cell 200 to be cultured in the apparatus. In various embodiments, the distance D between neighboring projections 144 is between about 5 micrometers and about 15 micrometers or between about 5 micrometers and 10 micrometers.

The projections 144 may extend from the major surface 149 of the structured surface 140 any suitable distance such that the cells 200 are effectively suspended above the major surface 149. For example, the projections may have a height h of greater than about 5 micrometers. In various embodiments, the projections 144 have a height h of between about 5 micrometers and about 25 micrometers.

The projections 144 of the structured surface 140 may be arranged in a regular or irregular pattern. For purposes of manufacturing, the projections 144 are arranged in a regular pattern or an array. Projections in an array may be of the same or difference shape, dimension, or configuration.

Figure 4:
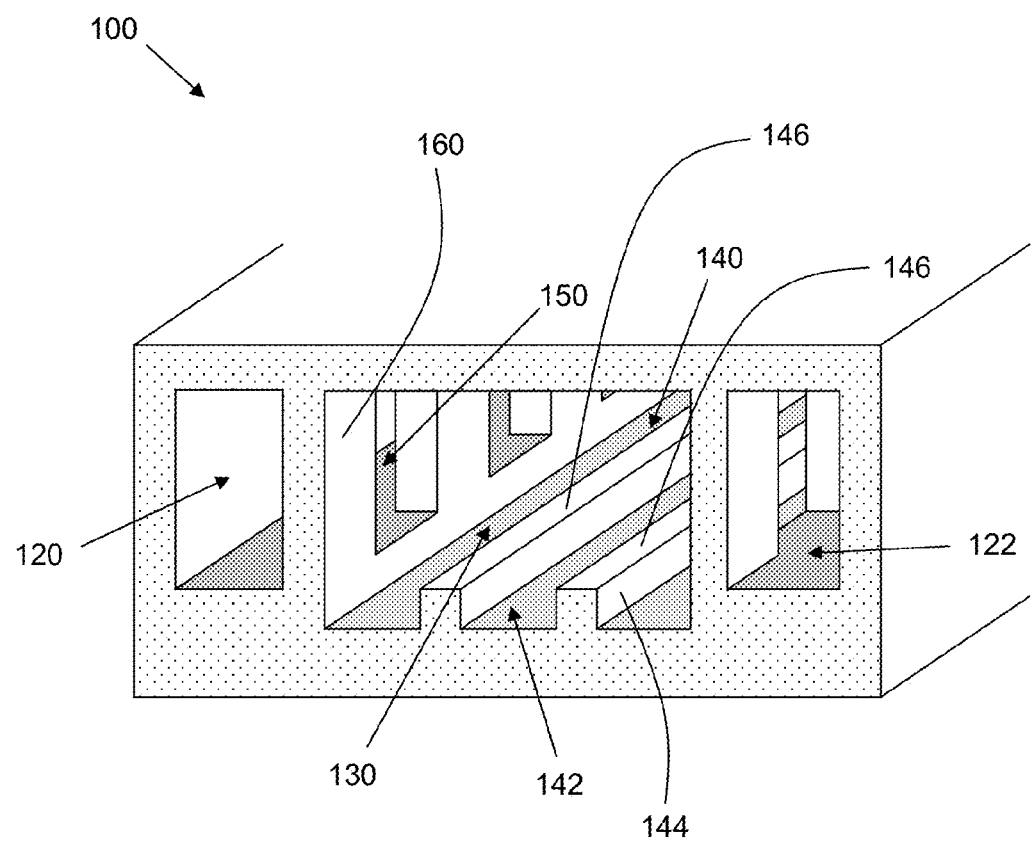
FIG. 4 is a schematic cutaway perspective view of an embodiment of a microfluidic device.
Figure 5:
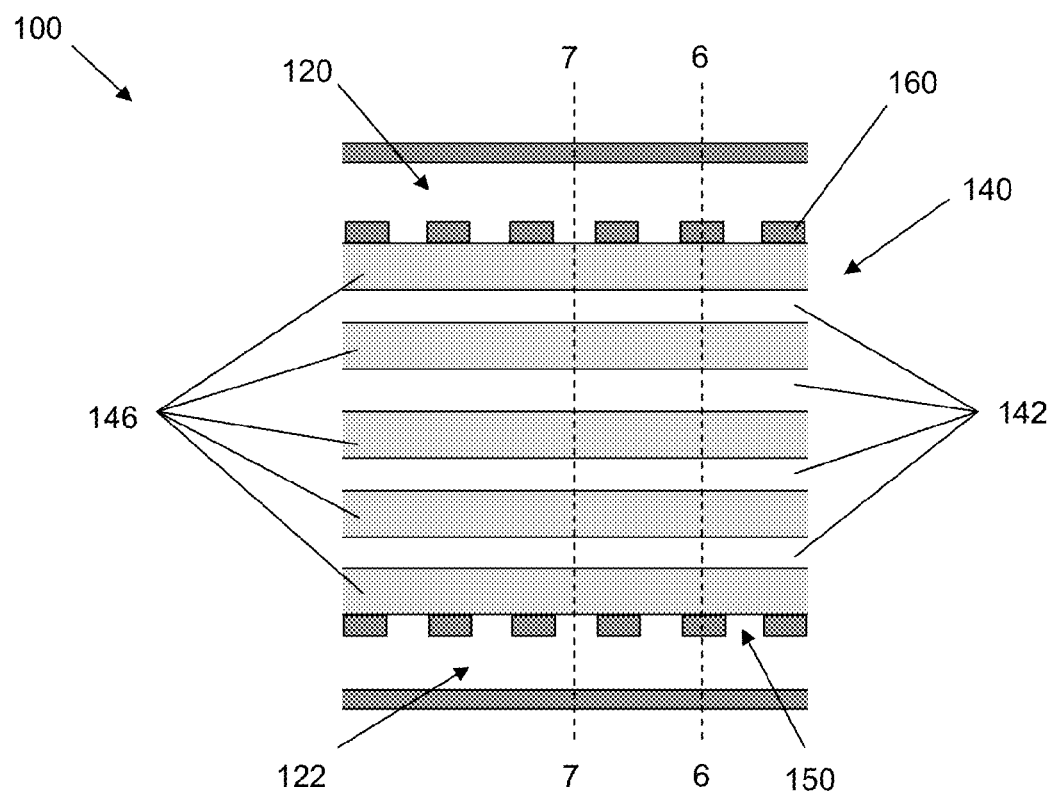
FIG. 5 is a schematic top down view of a portion of an embodiment of a microfluidic device.
Figure 6:
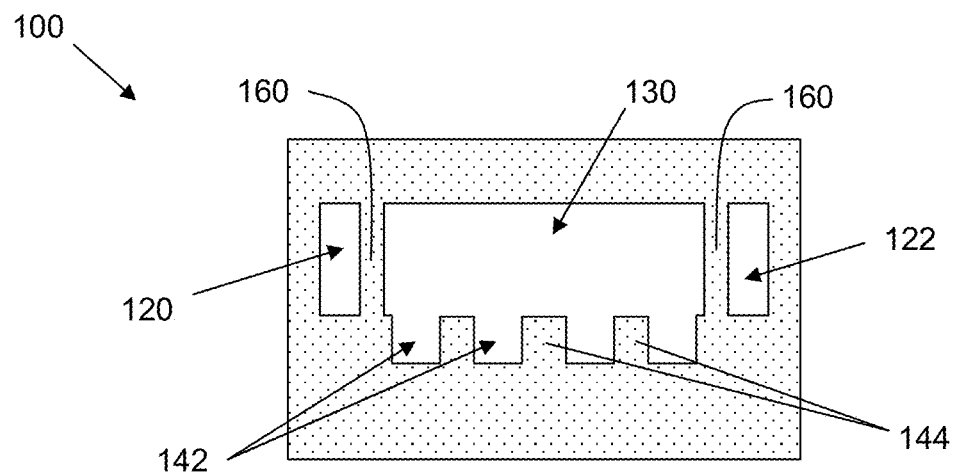
FIG. 6 is a schematic cross-section of the device shown in FIG. 5 taken along line 6-6.
Figure 7:
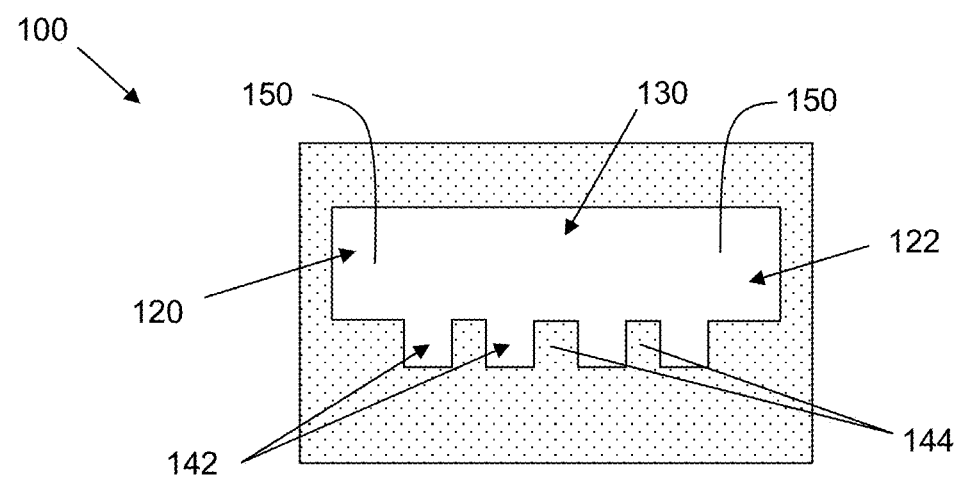
FIG. 7 is a schematic cross-section of the device shown in FIG. 5 taken along line 7-7.
Figure 8:
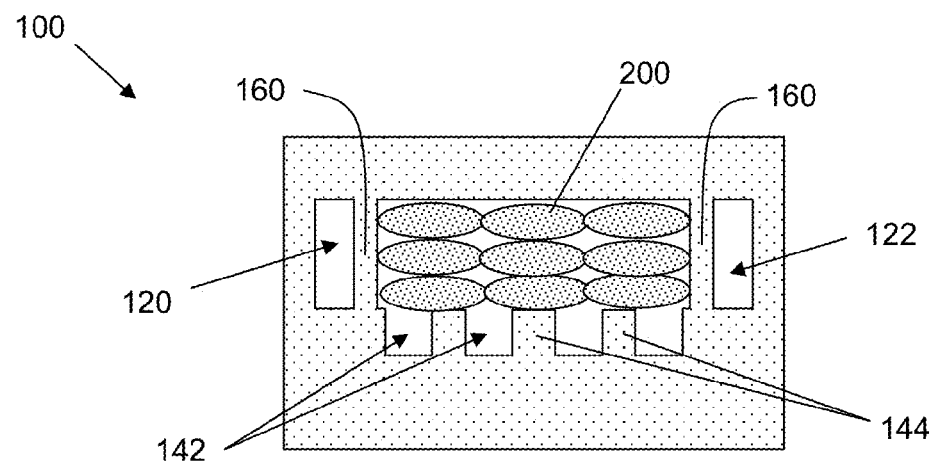
FIG. 8 is a schematic diagram of the device shown in FIG. 6 showing schematic cells cultured in the device.

Referring now to FIGS. 4-8, various views of embodiments of microfluidic devices 100 are shown. FIG. 4 is a schematic cutaway perspective view of an embodiment of a microfluidic device 100; FIG. 5 is a schematic top down view of a portion of an embodiment of a microfluidic device 100; FIG. 6 is a schematic cross-section of the device shown in FIG. 5 taken along line 6-6; FIG. 7 is a schematic cross-section of the device shown in FIG. 5 taken along line 7-7; and FIG. 8 is a schematic diagram of the device shown in FIG. 6 showing cells 200 cultured in the device 100.

In the embodiments depicted in FIGS. 4-8, the devices 100 include a cell retention chamber 130 into which cells 200 may be placed for culture. The chamber 130 may be of any suitable size to allow culture of a desired number of cells 200. In various embodiments, the chamber 130 is sized and configured to allow culture of two to six cells across the width and two to three cells across the height of the chamber. Having a width of two to six cells and a height of two to three cells allows for ready diffusion of nutrients or other agents from perfusion channels 120, 122 to the cells cultured in the chamber. It will be understood that the size of cells may vary depending on cell type and culture conditions. Accordingly, the appropriate size of the chamber 130 may be varied to provide for the desired number of cell width and height dimensions. It will also be understood that the size of cells of a given cell type under the same conditions may vary from cell to cell. Generally, when dimensions are described herein based on cell size, the dimensions are based on the average size of the cultured cells.

In various embodiments, the chamber 130 has a width of between about 80 and 120 micrometers (about 4 to 5 times the diameter of a typical cell, which is between about 20 and 25 micrometers), such as about 105 micrometers. The chamber 130 may be of any suitable height, e.g. between about 30 micrometers and 80 micrometers, between 35 and 50 micrometers, or about 45 micrometers. The chamber 130 may be of any suitable length, e.g., between about 100 micrometers and about 30,000 micrometers, between about 150 micrometers and about 20,000 micrometers, or between about 200 micrometers and about 15,000 micrometers. In many cases, a chamber 130 having a shorter length is more likely to be effectively packed with cells (if desired) relative to chambers having longer lengths.

The chamber 130 has a structured surface 140 that forms one or more troughs 142 between cell contacting surfaces 146. The troughs 142 are configured to provide channels for fluid retention or flow adjacent cells 200 cultured in the chamber 130. Accordingly, the troughs 142 are of a width that does not permit cells 200 cultured in the chamber 130 to block flow of fluid through the trough 142. That is, the widths of the troughs 142 are less than the width of the cells 200 to be cultured in the chamber 130. For example, the troughs 142 may be half the width of a cell 200 to be cultured. It will be understood that the width of the trough(s) 142 may be varied depending on the size of the cells 200 to be cultured in the apparatus 100. In various embodiments, the troughs have a width of less than about 15 micrometers, of between about 5 micrometers and about 15 micrometers or between about 5 micrometers and about 10 micrometers. In some embodiments, the troughs 142 have generally uniform widths along the length of the structured surface 140. In general, the troughs 142 are formed by the major surface (see, e.g., reference numeral 149 of FIGS. 2A-C) of the structured surface 140 and the sides of the projections 144. Accordingly, the troughs 142 may take any pathway along the major surface of the structured surface 140, depending on the shape and configuration of the projections 144. The troughs 142 extend the length of the structured surface 140.

The troughs 142 may be used to carry or retain fluid compositions that can deliver agents to the cells 200 or remove agents from the cell chamber 130. By way of example a composition comprising nutrients, such as a cell culture medium, may be placed in the troughs 142 to deliver nutrients to the cultured cells 200 or to remove waste products from the cells. Agents to be tested, such as pharmacologic agent, may be delivered to the cells 200 via the troughs 142. Agents that may induce cellular polarization, agents or compositions that mimic an in vivo physiological environment, or the like, may be introduced into the troughs 142. In various embodiments, culture of cells 200 in the chamber 130 fluidly isolates, at least partially, the troughs 142 from the perfusion channels 120, 122. For example, cells 200 cultured in the device 100 may interact to form a tissue-like morphology with cell-cell interactions that can inhibit or reduce bulk movement of fluid between the troughs 142 and the perfusion channels 120, 122

Still with reference to FIGS. 4-8, the depicted devices 100 include first 120 and second 122 perfusion channels through which fluid may flow. In various embodiments (not shown), a device includes one or more than two perfusion channels. The channel includes retention posts 160 forming openings 150 that provide for fluid communication between the chamber 130 and the perfusion channels 120, 122, allowing diffusion of agents between the perfusion channels 120, 122 and the cell chamber 130 via the openings 150. The openings 150 are of dimensions to prevent cells in the chamber 130 from entering a perfusion channel 120, 122. For example, the openings 150 may have a height, width or diametric dimension of less than about 20 micrometers, less than about 15 micrometers, less than about 10 micrometers or about 5 micrometers. While shown in FIGS. 4-8 as having a rectangular cross-sectional shape, it will be understood that retention posts 160 may be of any suitable shape or configuration. In various embodiments, the retention posts 160 have an ellipsoid, circular, triangular, w-shaped, or irregular cross-sectional shape, or the like.

The perfusion channels 120, 122 may be of any suitable dimension. In various embodiments, the height of a perfusion channel 120, 122 is the same as the height of the cell retention chamber 130, and in some embodiments the height of a perfusion channel 120, 122 is the different than the height of the cell retention chamber 130. In embodiments, the first and second perfusion channels, 120, 122, are configured to carry fluid such as cell culture medium. In embodiments, the first and second perfusion channels 120, 122 are configured to prevent cells from entering the perfusion channels 120, 122 from the cell retention chamber 130. In some embodiments, the height of a perfusion channel is between about 30 micrometers and about 80 micrometers, between about 35 and about 50 micrometers, or about 45 micrometers. It may be desirable for the width of the perfusion channel to be greater than or equal to about 1.5 times the diametric dimension of cells cultured in the device so that if a cell happens to enter the perfusion channel, the cell will pass through the channel without blocking flow. In some embodiments, the width of a perfusion channel is between about 30 micrometers and about 1000 micrometers, between about 30 micrometers and about 100 micrometers, or between about 30 micrometers and about 45 micrometers. Typically, the perfusion chamber 120, 122 runs along side of the cell retention chamber 130 along the length of the chamber.

Figure 9A:
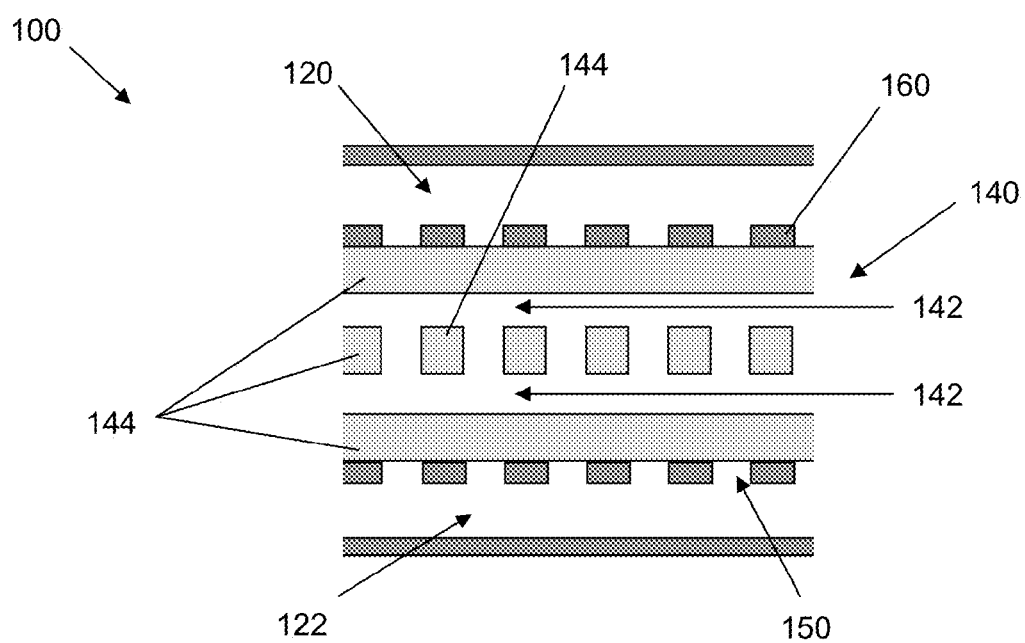
FIGS. 9A-B are schematic top down views of portions of embodiments of microfluidic devices.
Figure 9B:
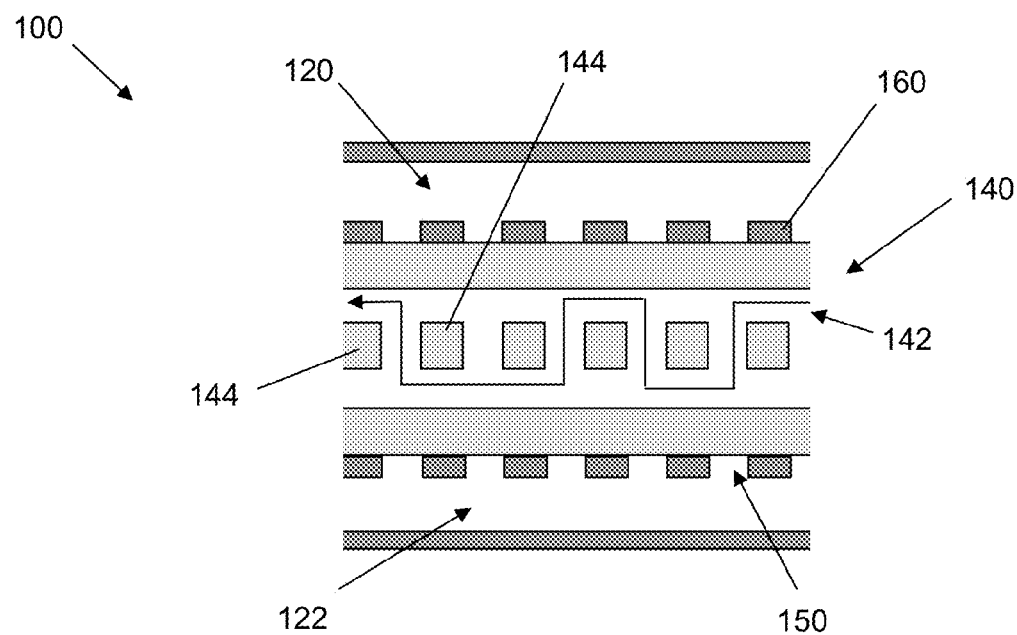

Referring now to FIGS. 9A-B, schematic top down views of portions of embodiments of microfluidic devices 100 are shown. The devices 100 are similar to the device shown in FIG. 5, with like reference numbers referring to like parts or components. Some of the projections 144 shown in FIG. 9A-B are square pillars rather than elongate projections as shown in FIG. 5 (of course, some of the projections in FIGS. 9A-B are elongate projections). The projections 144 depicted in FIGS. 9A-B form at least a portion of a trough 142 that runs the length of the structured surface 140. As shown by the line in FIG. 9B, the trough 142 may be of any suitable shape and may be considered to take any suitable path along the length of the structured surface 140. When at least some of the projections 144 allow for a trough 142 to take more than one path, the trough 142 may be considered to take any suitable path.

Regardless of the structure of the trough(s) and projections, the structured surface, in various embodiments, is configured to restrict the spreading of cells, which may promote three-dimensional tissue-like morphology and cell-cell interaction. The configuration of the structured surface, and thus the shape and configuration of the projections and path and configuration of the trough(s), may be varied depending on the cells to be cultured so that the desired effects (e.g., 3D tissue-like morphology) are achievable. In general, it is desired that the projections 144 facilitate virtual suspension of cells cultured in the chamber. The projections 144 and the trough(s) 142 together may facilitate virtual suspension of cells, where the cells rest on top of the projections and fluid within the trough(s) assists in suspending the cells. By creating such virtual suspension, it is believed that controlled cell aggregation or rearrangement of cells into tissue-like architecture can be promoted.

Figure 10:
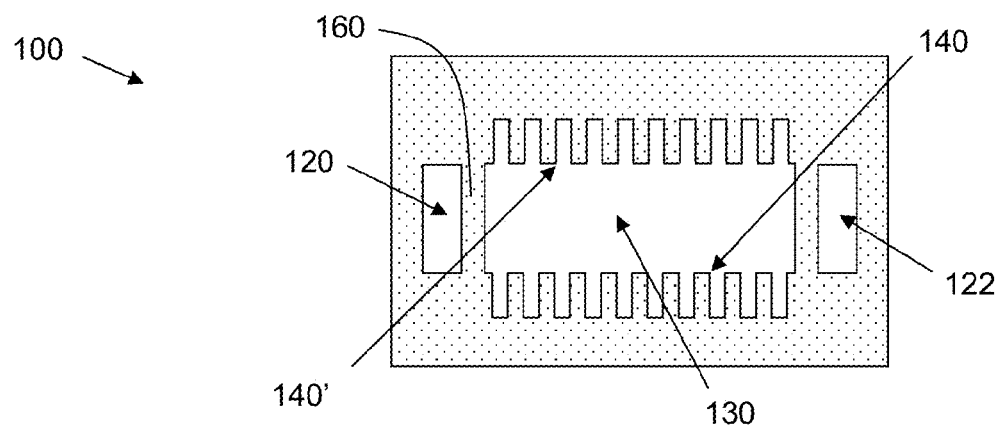
FIG. 10 is a schematic cross-section of an embodiment of a microfluidic device.

As shown in FIG. 10, the top and bottom surfaces of the cell retention chamber may be structured surfaces 140, 140'. By providing structured surfaces 140, 140' at both the top and bottom of the chamber 130 interaction of the device 100 with cells cultured in the device can be further minimized (relative to only one surface). In addition, the side surfaces of the chamber 130 are effectively formed by the retention posts 160 and openings of the perfusion channels 120, 122, which are effectively structure surfaces as well. When the chamber 130 is packed with cultured cells, the top structured surface 140' may form channels, along with the cells, through which fluid may flow. That is, cells in culture may form a seal between projections, forming a sealed channel through which fluid such as cell culture media may flow. In embodiments, these cell-formed sealed channels may allow for the delivery of fluid to one side of cells in culture, separate from the fluid delivered to another side of cells in culture, thereby allowing cells to establish polarity in culture, when they are exposed to a different fluid on one side versus another side.

Figure 11:
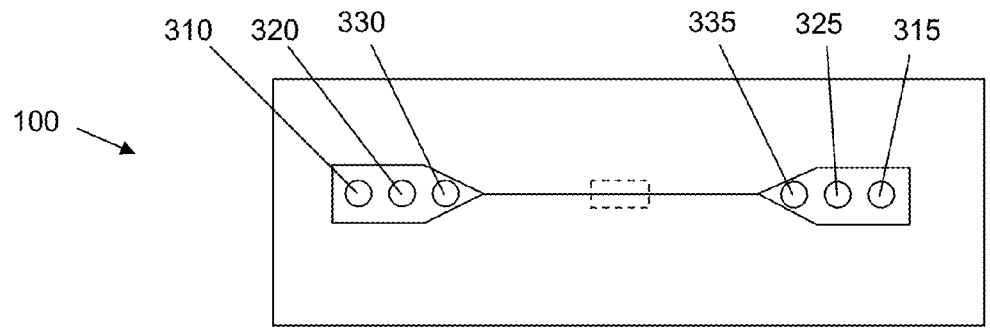
FIGS. 11-12 are schematic top-down views of embodiments of devices.
Figure 12:
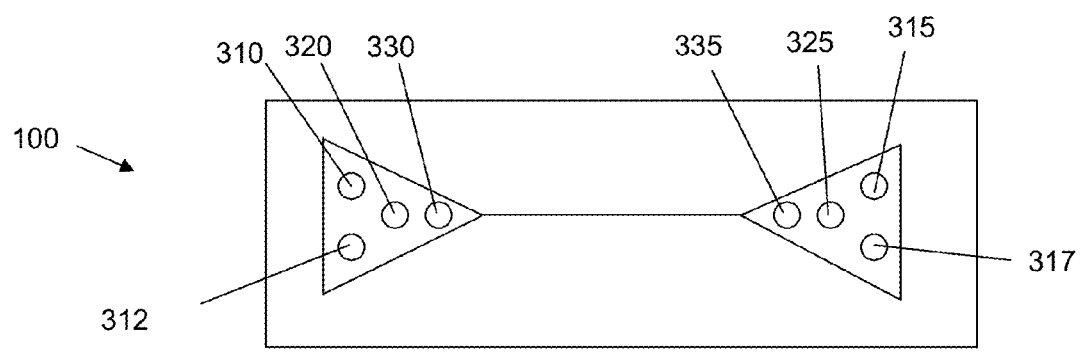

Referring now to FIGS. 11-12 schematic top-down views of embodiments of devices 100 are shown. Inlets 310, 312, 320, 330 and outlets 315, 317, 325, 335 are shown. The inlets and outlets are accessible from the exterior of the device 100. A microfluidic device as described herein may include any suitable number of inlets and outlets. It will be understood that an inlet may serve as an outlet and an outlet may serve as an inlet, depending on the direction of fluid flow. In the embodiment depicted in FIG. 11, the device 100 has a perfusion channel inlet 310, a trough inlet 320, a cell chamber inlet 330, a perfusion channel outlet 315, a trough outlet 325, and a cell chamber outlet 335. The area depicted in the dashed box in FIG. 11, is a schematic representation of the area of the device shown in, e.g., FIG. 5. The perfusion channel inlet 310 and outlet 315 are in fluid communication with the perfusion channels 120, 122 (e.g., as depicted in FIG. 5) and allow fluid to enter the inlet 310 flow through the perfusion channels 120, 122 and exit the outlet 315. In the embodiment depicted in FIG. 12, inlet 310 and outlet 315 are in fluid communication with one perfusion channel 120 (e.g., as depicted in FIG. 5); and inlet 312 and outlet 317 are in fluid communication with another perfusion channel 122 (e.g., as depicted in FIG. 5). Thus, independent control of the content, rate, and direction of the flow within a perfusion channel can be achieved.

In the embodiments depicted in FIGS. 11-12, the trough inlet 320 and trough outlet 325 are in fluid communication with one or more troughs 142 (e.g., as depicted in FIG. 5). Of course, one or more inlets and outlets may be employed if it is desired to independently control the content rate or direction of flow of fluid in a given trough or troughs. In the depicted embodiments, the cell chamber inlet 330 and outlet 335 are in fluid communication with the cell chamber. Accordingly, depending on the number of inlets and outlets provided, the composition, rate or direction of flow may be varied as desired between perfusion channels and troughs.

Figure 13A:
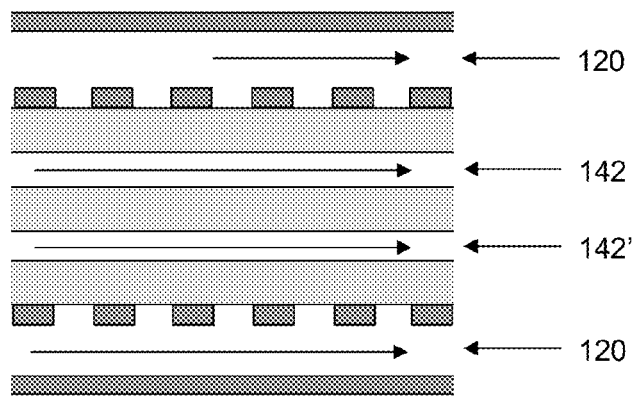
FIGS. 13A-C are schematic top-down views of portions of microfluidic devices showing examples of fluid flow.
Figure 13B:
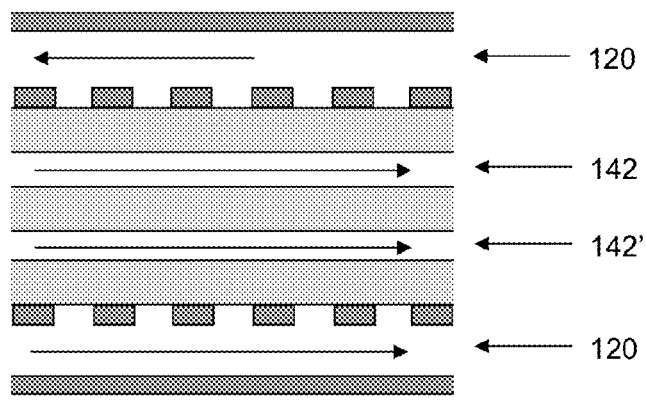
Figure 13C:
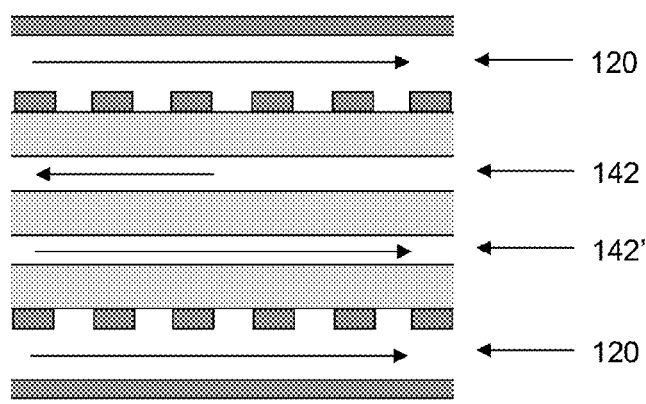

By way of example and with reference to FIGS. 13A-C, examples of flow through a representative microfluidic device are shown. The direction of flow is indicated by the arrows in the perfusion channels 120, 122 and the troughs 142, 142'. The rate of flow is indicated by the length of the arrows. The same of different fluid compositions may be introduced into perfusion channels 120, 122 and the troughs 142, 142'. In some embodiments, the direction of flow in a channel or trough may be changed, the rate of flow may be changed, or the composition of the fluid flowing through a channel or trough may be changed at any desired time.

Pumps, syringes, or other suitable injection or infusion device may be employed to introduce fluid into an inlet in communication with a cell chamber, trough or perfusion channel. The microfluidic devices described herein can readily be adapted for use with available robotic fluid handling systems.

The configuration of the structured surface(s) and the perfusion channels, as well as the composition, direction, and rate of flow can be varied in microfluidic devices, as described herein, as desired to achieve a suitable device that closely mimics in vivo tissue conditions.

In many embodiments, the flow through the perfusion channels or troughs is configured to be laminar, which as used herein means that the direction of flow at any given point in the channel or trough is generally in the same direction. Alternatively, laminar flow, for purposes of the present disclosure, can be considered as non-turbulent. Due to microfluidic nature of the device and pressure driven flows used for device perfusion pressure drops may develop along the perfusion channels as well as trough. As the length of the chamber increases the flow resistance will increase, obstructing the independent flows in troughs and perfusion channels. Thus the dimensions of the chamber may vary depending on the desired flow characteristics. For example, in some situations flow in a trough in a direction generally opposite that of a perfusion channel may be achievable across a chamber length of 500 micrometers but may not be achievable across a chamber length of 1500 micrometers.

Referring now to FIG. 14A-E, an embodiment of a microfluidic apparatus is shown. In the top panel (FIG. 14A) a schematic overview is shown; in the middle panels (FIGS. 14B-C) magnified images of a representative are shown; and in the lower panels (FIGS. 14D-E) images at higher magnification are shown. In the depicted embodiment, the first 120 and second 122 perfusion channels extend beyond the cell culture chamber 130 to the inlets 310, 312 and outlets 315, 317. The structured surface 140 also extends beyond the cell chamber 130 to inlet 320 and outlet 325. Inlet 330 is in fluid communication with chamber 130 and provides access for introduction of cells into chamber 130. In the depicted embodiment, retention posts 131 are positioned at one end of the chamber to prevent cells introduced into the chamber 130 from migrating past the retention posts 131 towards outlet 335, which is also in fluid communication with the chamber 130. It will be understood that an inlet may be an outlet and an outlet may be an inlet, depending on the direction of fluid flow.

Figure 14:
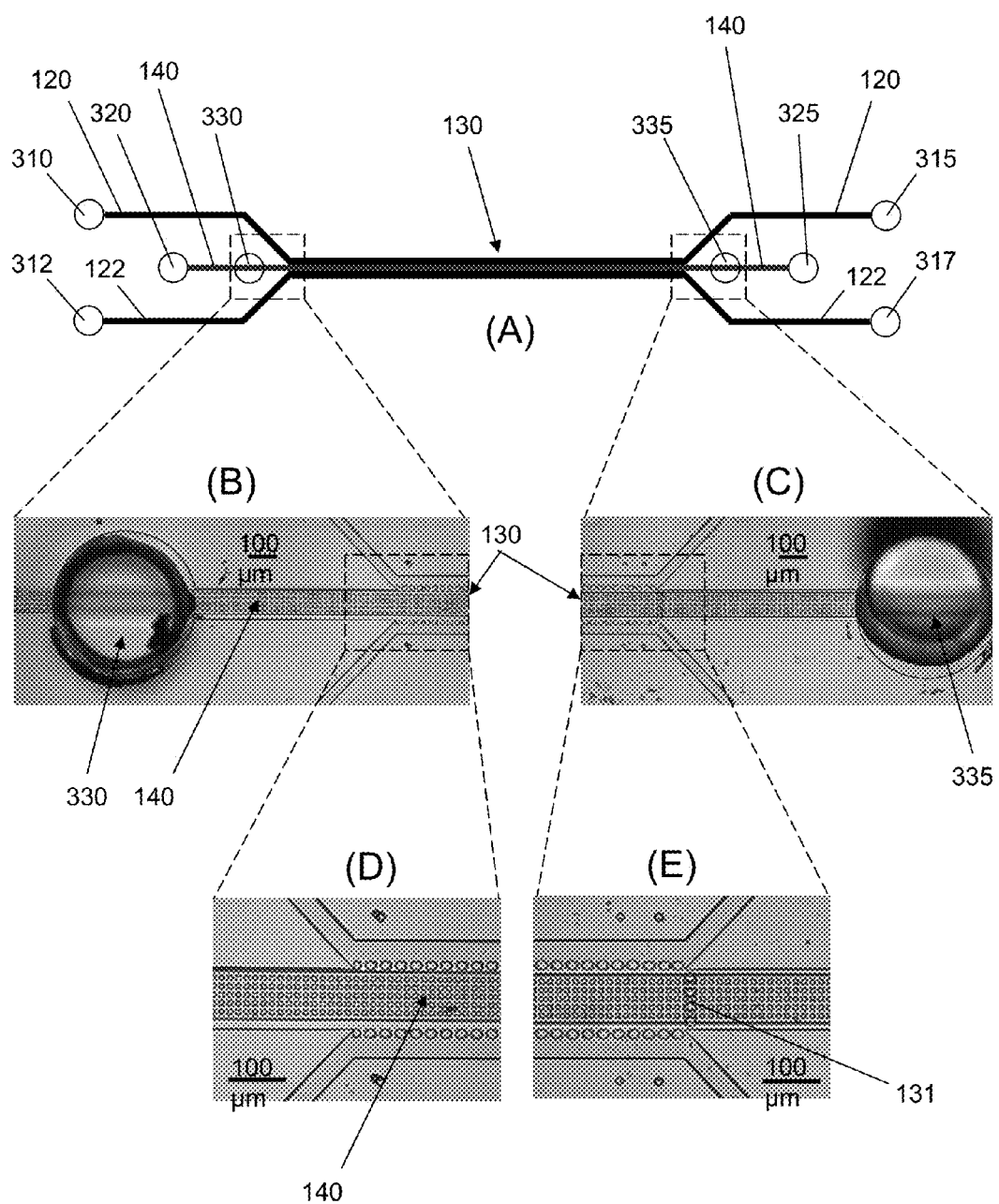
FIGS. 14A-E show a schematic diagram of an embodiment of a microfluidic apparatus (A), magnified images of portions of a microfluidic apparatus (B-C), and images at higher magnification (D-E).
Figure 15:
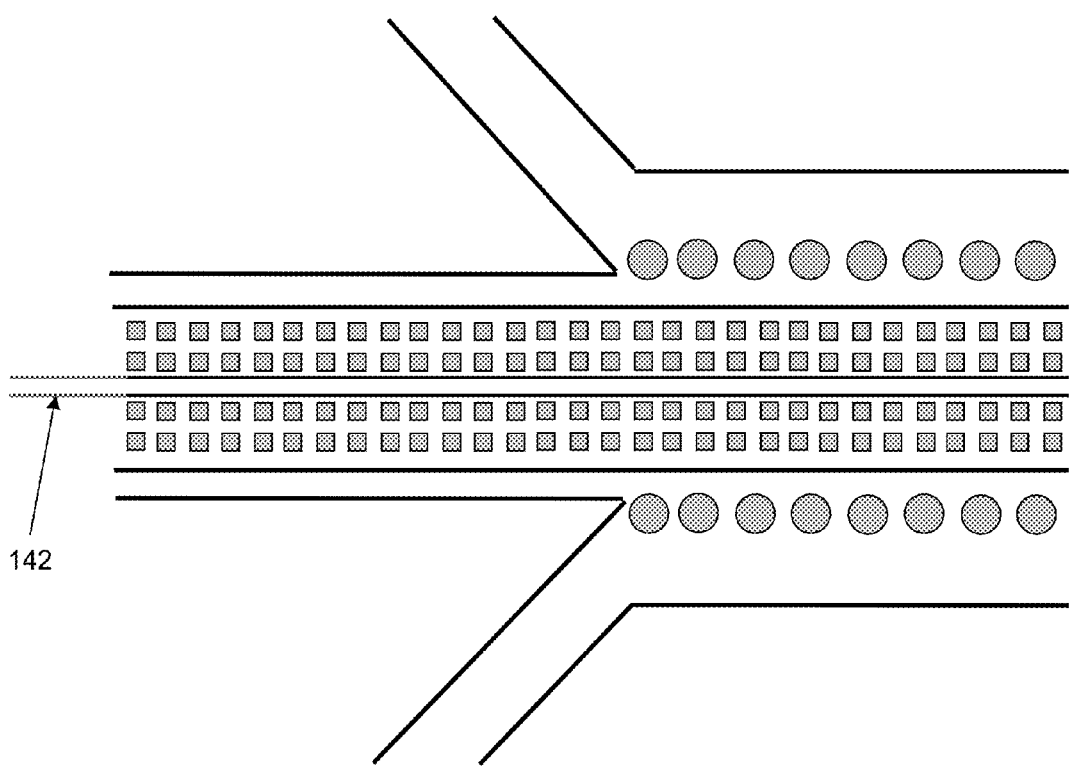
FIG. 15 is a schematic top down view of a portion of an embodiment of a microfluidic apparatus.

Referring now to FIG. 15, an alternative embodiment of a portion of a microfluidic cell culture apparatus is shown. In the depicted embodiment, a linear trough 142 extends beyond the structured surface and is in fluid communication with an inlet (as opposed to the entire structured surface, as shown in FIG. 14). In such embodiments, where troughs leading into the structured surface, rather than the entire width of the structured surface, are operably coupled to an inlet, the likelihood that cells cultured on the structured surface can form a tight seal and fluidly isolate the trough from the perfusion channels is increased because, the area over which the cells need to form a tight seal to accomplish the isolation is reduced (over the trough rather than over the entire width of the structured surface). Further, gradients of agents introduced through the trough in such embodiments may be achieved not only from the bottom to the top of the cell culture chamber, but also from the center to the sides of the cell culture chamber.

A microfluidic device may be made from any suitable material or materials and may be formed via any suitable technique. For example, a microfluidic device, or portion thereof, may be formed via a master, such as a silicon master. The master may be fabricated from silicon by proximity U.V. photolithography. By way of example, a thin layer of photoresist, an organic polymer sensitive to ultraviolet light, may be spun onto a silicon wafer using a spin coater. The photoresist thickness is determined by the speed and duration of the spin coating. After soft baking the wafer to remove some solvent, the photoresist may be exposed to ultraviolet light through a photomask. The mask's function is to allow light to pass in certain areas and to impede it in others, thereby transferring the pattern of the photomask onto the underlying resist. The soluble photoresist is then washed off using a developer, leaving behind a protective pattern of cross-linked resist on the silicon. At this point, the resist is typically kept on the wafer to be used as the topographic template for molding the stamp. Alternatively, the unprotected silicon regions can be etched, and the photoresist stripped, leaving behind a wafer with patterned silicon making for a more stable template. The lower limit of the features on the structured substrates is dictated by the resolution of the fabrication process used to create the template. This resolution is determined by the diffraction of light at the edge of the opaque areas of the mask and the thickness of the photoresist. Smaller features can be achieved with extremely short wavelength UV light (~200 nm). For submicron patterns (e.g. etch depths of about 100 nanometers), electron beam lithography on PMMA (polymethylmetacrylate) may be used. Templates can also be produced by micromachining, or they can be prefabricated by, e.g., diffraction gratings.

To enable simple demoulding of the master, an anti-adhesive treatment may be carried out using silanization in liquid phase with OTS (octadecyltrichlorosilane) or fluorinated silane, for example. After developing, the wafers may be vapor primed with fluorinated silane to assist in the subsequent removal of the array of projections. Examples of fluorinated silane that may be used include, but are not limited to, (tridecafluoro-1,1,2,2-tetrahydroctyl) trimethoxysilane, and tridecafluoro-1,1,2,2-tetrahydrooctyl) triethoxysilane.

Figure 16:
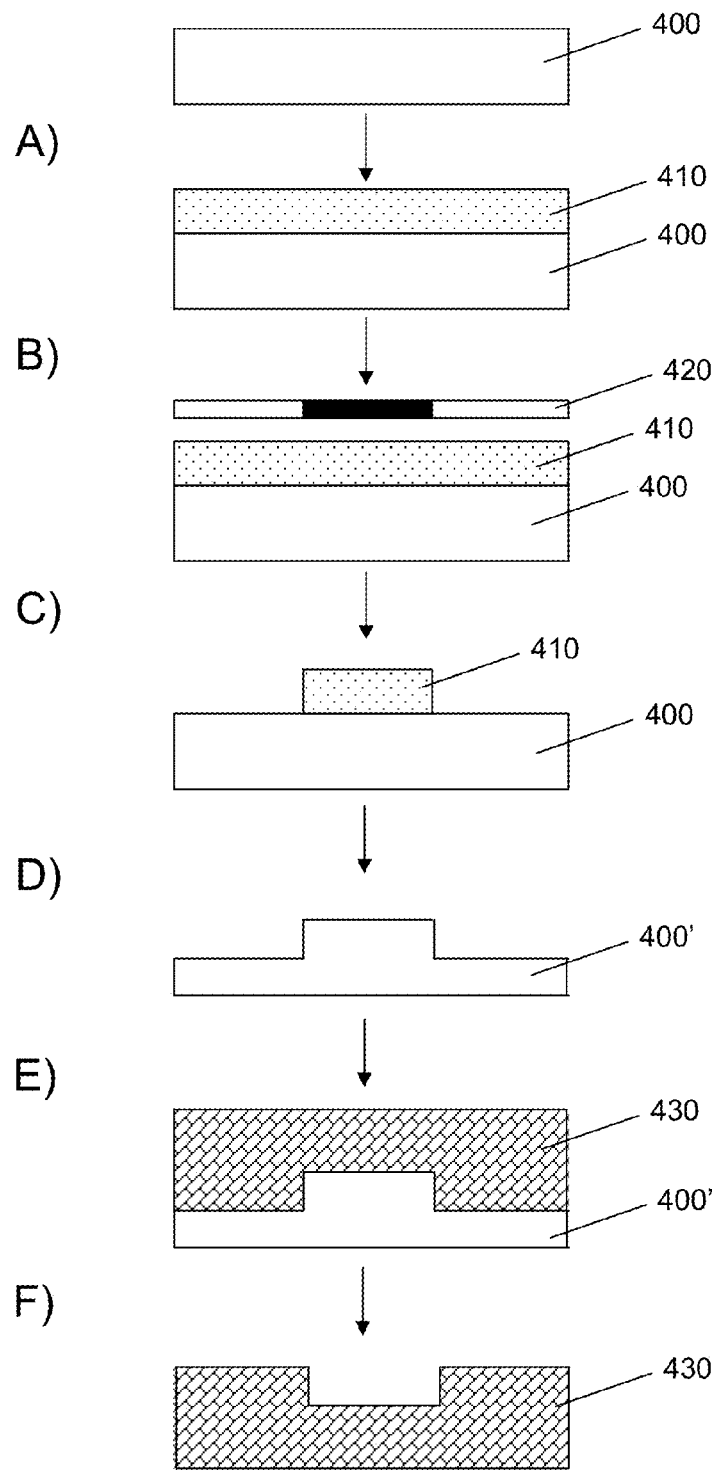
FIGS. 16A-F are a schematic illustration of a photolithographic process for preparing a device or portion thereof.

By way of example and with reference to FIG. 16, an outline of a process for forming a device or portion thereof is illustrated. As shown in FIG. 16, a photoresist 410 is coated on a silicon wafer 400 (A). A photomask 420, such as a chromium mask, is then placed over the photoresist (B) and the resulting assembly subjected to UV radiation. Areas of the photoresist 410 exposed to UV are washed away (C) and the resulting structure is etched (D) to produce the silicon master 400', which is replication molded with a polymer 430, such as polydimethylsiloxane (PDMS).

In some embodiments, hot embossing or injection molding may be used to form the resulting polymer. However, the silicon master may not hold up well under conditions for such processes. In such cases, a reverse silicon master can be made and a metal, such as nickel, may be deposited on the reverse master to create a metal master for use in such processes.

Any suitable material or materials may be used to form the microfluidic device or components thereof. For example, the device or components thereof may be fabricated from inorganic materials including glass, silica, silicon, metal, or the like or plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers and copolymers including copolymers of norbornene and ethylene, fluorocarbon polymers, polystyrenes, polypropylene, polyethyleneimine; copolymers such as poly (vinyl acetate-co-maleic anhydride), poly(styrene-co-maleic anhydride), polysaccharide, polysaccharide peptide, poly (ethylene-co-acrylic acid) or derivatives of these or the like. The materials for forming the devices or components or parts thereof may be selected based on desired mechanical, cell-interacting, or other properties for optimizing cell culture for distinct types of cells.

Figure 17A:
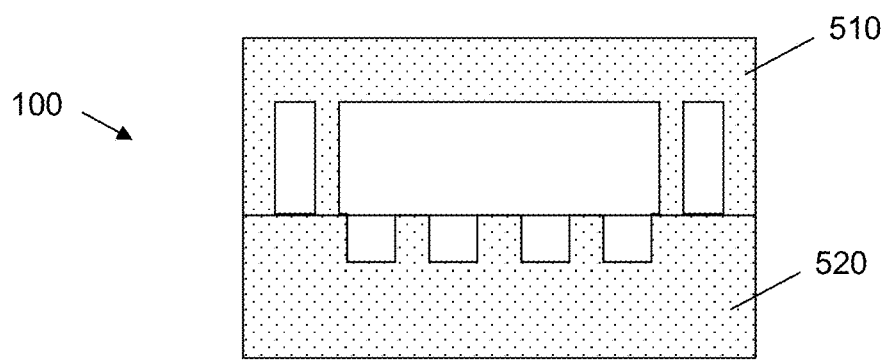
FIGS. 17A-B are schematic cross sections of microfluidic devices formed from top part and bottom parts.
Figure 17B:
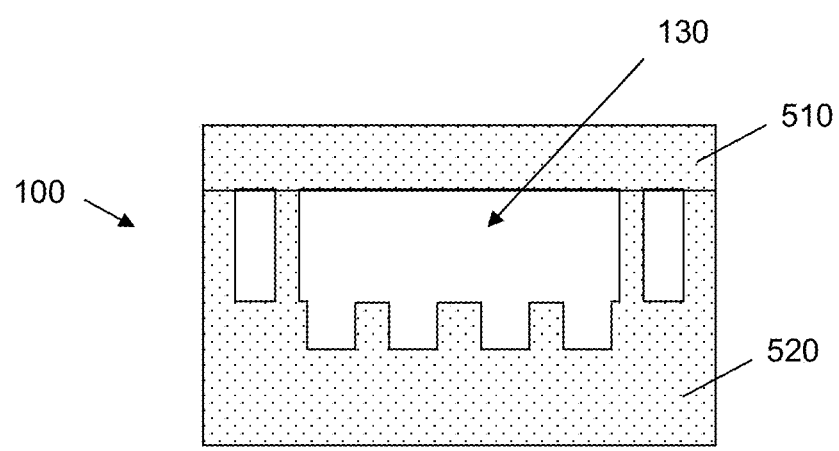

In various embodiments, a device is formed from two parts. For example and with reference to FIGS. 17A-B, the device 100 may be formed from a top part 510 and a bottom part 520. In the device 100 depicted in FIG. 17A, the top 510 and bottom 520 parts are carefully aligned prior to joining. In the device 100 depicted in FIG. 17B, the top part 510 is a plate, lid, cover, or the like that may be sealingly joined to the bottom part 520. The top part 510 may include inlets and outlets. Depending on the material used to form the top part 510 or the bottom part 520, the parts may be self sealing. Otherwise, the parts may be adhered, welded, or the like to sealingly engage.

The cell retention chamber 130 (see e.g., FIG. 17A) or a portion thereof may be treated or coated to impart a desirable property or characteristic to the treated or coated surfaces.

Examples of surface treatments often employed for purposes of cell culture include corona or plasma treatment. In various embodiments, projections or substrate surfaces are coated with a polysaccharide, such as a galactomannan, an alginate, or the like, or are coated with extracellular matrix (ECM) materials, such as naturally occurring ECM proteins or synthetic ECM materials. The type of EMC selected may vary depending on the desired result and the type of cell being cultures, such as a desired phenotype of the culture cells. Examples of naturally occurring ECM proteins include fibronectin, collagens, proteoglycans, and glycosaminoglycans. Examples of synthetic materials for fabricating synthetic ECMS include polyesters of naturally occurring α-hydroxy acids, poly(DL-lactic acid), polyglycolic acid (PGA), poly(-lactic acid) (PLLA) and copolymers of poly(lactic-co-glycolic acid) (PLGA). Such thermoplastic polymers can be readily formed into desired shapes by various techniques including moulding, extrusion and solvent casting. Aminoacid-based polymers may also be employed in the fabrication of an ECM for coating a projection or substrate. For example, collagen-like, silk-like and elastin-like proteins may be included in an ECM. In various embodiments, an ECM includes alginate, which is a family of copolymers of mannuronate and guluronate that form gels in the presence of divalent ions such as $Ca^{2+}$. Any suitable processing technique may be employed to fabricate ECMs from synthetic polymers. By way of example, a biodegradable polymer may be processed into a fiber, a porous sponge or a tubular structure.

One or more ECM material may be used to coat the projections or substrates. For example, in embodiments, cell adhesion factors, such as polypeptides capable of binding integrin receptors including RGD-containing polypeptides, or growth factors can be incorporated into ECM materials to stimulate adhesion or specific functions of cells using approaches including adsorption or covalent bonding at the surface or covalent bonding throughout the bulk of the materials. It will be understood that the type of cell or cells to be cultured in the cell retention chamber may play a role in determining which treatment or coating, if any, may be applied to projections or other portions of the cell chamber. In many embodiments, no coating is applied to the cell culture chamber 130 or a portion thereof.

Microfluidic cell culture articles having structured surfaces as described above may be used to culture a variety of cells and may provide important three dimensional structure to impart desirable characteristics to the cultured cells. Any type or combination of types of cells (e.g., liver cells, stem cells, kidney cells, cardiac cells, neuronal or glial cells, or the like) may be cultured in such microfluidic cell culture articles.

Figure 18:
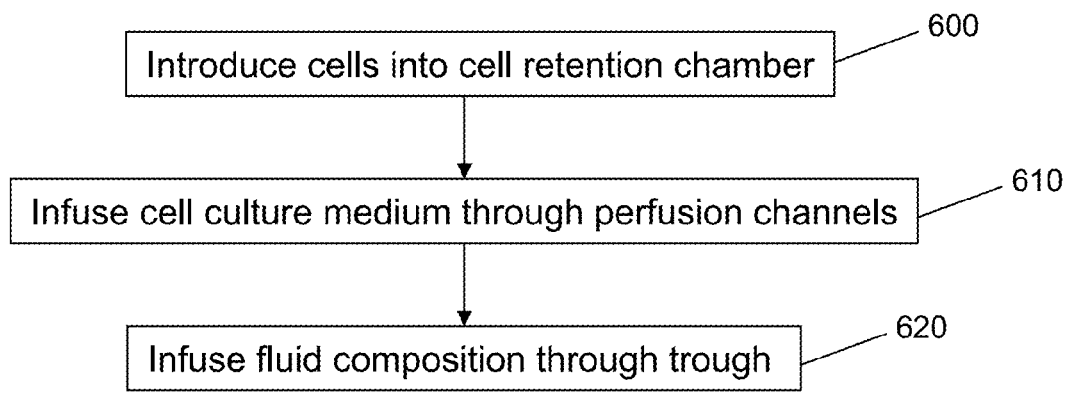
FIGS. 18-19 are flow diagrams of overviews of methods.
Figure 19:
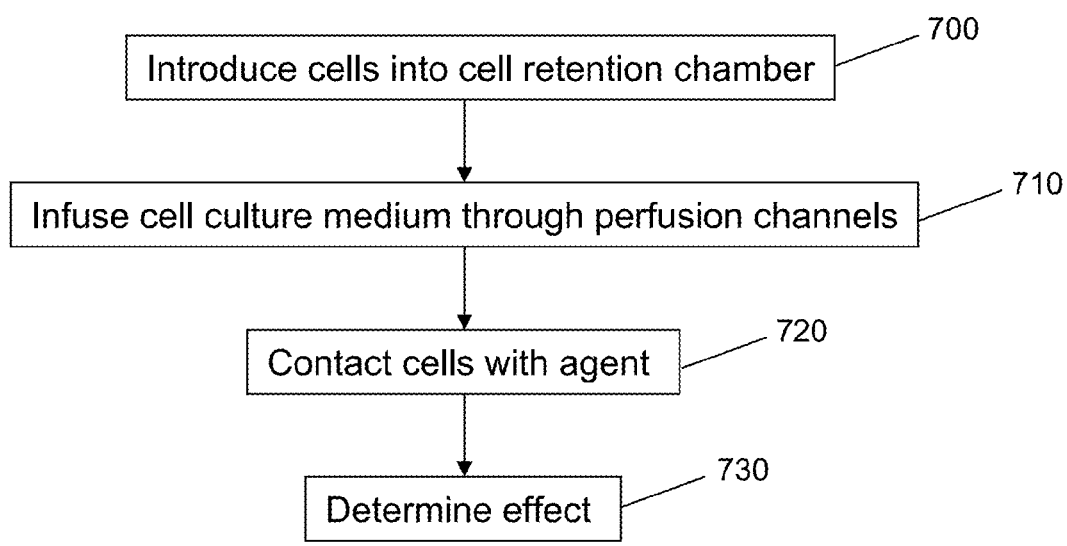

Referring now to FIGS. 18-19, general overview of methods that may be employed using microfluidic devices as described herein are shown. In the method shown in FIG. 18, cells are introduced into the cell retention chamber (600), e.g. by infusing cells into the chamber via a cell chamber inlet. In many embodiments, a sufficient number of cells are introduced into the chamber to pack the chamber with cells. While the number of cells to pack the chamber may vary depending on the type of cell or cells used, between about 5000 and about 15000 hepatocytes are sufficient to pack a chamber having a volume of 0.06 mm³. In some embodiments, a number of cells less than the number of cells that would pack the chamber are introduced into the chamber. The cells may be cultured in a manner that would allow proliferation to pack the chamber or may be cultured in manner such that the chamber does not become packed. The number of cells added and whether the chamber is packed may depend on the cells being cultured, the effect to be studied, or the like. After the cells are introduced into the cell retention chamber (600), cell culture medium may then be infused via the perfusion channels (610). After a sufficient time (e.g., until the cells from tight junctions, which can take about 3 days for hepatocytes), fluid may then be infused through the trough (620) to produce a desired effect or to study the effect.

With reference to FIG. 19, the microfluidic devices described herein may be used to determine the effect of various agents, such as small molecule pharmacological agents or biologic agents, on cells or the effect of cells on the agents. Similar to the method depicted in FIG. 18, the cells are introduced into the cell retention chamber of the device (700) and cell culture medium is infused trough the perfusion channel(s) (710). After a sufficient time of culture, an agent may be contacted with the cells (720). The agent may be introduced via the perfusion channel(s), trough(s), or cell retention chamber. The effect of the cells on the agent, the agent on the cells, or the like may be determined after a suitable time of incubation of the agent with the cells (730). In some embodiments, sensors, markers, or appropriate readers are incorporated into the device so that the effect may be determined. In various embodiments, fluid or cells are collected from the device, and the fluid is analyzed to determine the effect of the cells on the agent, of the agent on the cells, or the like. The fluid may be collected from the perfusion channel(s), trough(s), or cell retention chamber.

As described in more detail in the Examples below, microfluidic cell culture articles having structured surfaces have been shown herein to result in cultured hepatocytes having restored polarity and in vivo-like functions. In vitro cultured hepatocytes are popular for drug metabolism and toxicity studies. However, hepatocytes cultured on conventional two-dimensional cell culture substrates rapidly loose their polarity and their ability to carry out drug metabolism and transporter functions. To improve the ability to maintain drug metabolism and transporter functions, hepatocytes have been cultured in well established in vitro models including (i) culturing on MATRIGEL™ (BD Biosciences), an animal derived proteineous matrix, and (ii) culturing in a sandwich culture system between two layers of ECM such as collagen. However, such systems suffer from significant drawbacks including the potential for phage contamination of the human hepatocytes due to animal origin of the MATRIGEL™ or ECM materials, complex molecular compositions, batch-to-batch variations and uncontrollable coating. Culturing hepatocytes in microfluidic devices as described herein may overcome one or more of the drawbacks of prior systems.

Any hepatocyte cell may be cultured in a microfluidic device as described herein. For example, the hepatocytes to be cultured may be human or non-human (e.g., rat, pig, etc.) hepatocytes. Examples of human hepatocytes that may be cultured include human HepG2 cells, human HepG2C3A cells, immortalized FaN4 cells, human primary liver cells, or the like, or combinations thereof. The hepatocytes may be seeded in a cell culture chamber of a microfluidic device at any suitable density. To pack the chamber, hepatocytes may be seeded at a density of between about 100,000 cells per microliter of the chamber and about 200,000 cells per microliter of the chamber. The seeding density can be optimized, based on culture conditions and duration. For example, for long term culture, the seeding density can be lower (e.g., 30,000 cells to 50,000 cells per microliter of the chamber).

In some embodiments, cells capable of proliferation, such as hepG2 cells, are seeded at a density lower than that which packs the chamber, and the cells may be allowed to proliferate to pack the chamber. In various embodiments, non-proliferating cells, such as primary hepatocytes, are seeded at a density that packs the cell chamber.

Any suitable incubation time and conditions, regardless of the cell type, may be employed. It will be understood that temperature, $CO_2$ and $O_2$ levels, culture medium content, and the like, will depend on the nature of the cells being cultured and can be readily modified. The amount of time that the cells are incubated in the cell retention chamber may vary depending on the cell response being studied or the cell response desired. Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. The optimal culture medium for each type of cells, such as recommended by American Tissue Cell Culture or other suppliers, can be used with or without modifications.

While not shown herein, it will be understood that microfluidic devices as described herein may readily be multiplexed for throughput to a multi-device chip format. By way of example, such a multi-device chip format may have a footprint of a conventional 96 well plate.

In the following, non-limiting examples are presented, which describe various embodiments of the articles and methods discussed above.

EXAMPLES

Example 1

Device Fabrication and Assembly

Four inch silicone wafers were primed with P-20 (Microprime Primer P-20, Shin-Etsu MicroSi, Phoenix, Ariz.), and a 1 um thick Shipley 1813 photoresist (Rohm and Haas, Philadelphia, Pa.) was spun on the wafer at 3000 rpm for 30 sec (acceleration 1000 rpm/s) and soft baked on a hot plate for 1 min at 110° C. The wafers were exposed to UV-light through a chromium mask with the desired structures designed as CAD-drawing using MA6 (Karl Suss) mask aligner. After post bake of 2 min at 80° C. the wafers were finally developed (60-100 s, MF-319, Shipley), thoroughly rinsed with water and dried. Molds for 15 um deep troughs and 45 um deep fluidic channels and cell culture chamber were etched into the silicone using Plasma Therm 72 fluorine based reactive ion etcher. After photoresist stripping and cleaning silicone masters were exposed to trichloro(1H, 1H, 2H, 2H)-perfluorooctyl vapor for 2 h for passivation. Polydimethylsiloxane (PDMS) replicas were produced by pouring a precursor mixture over the whole 4" (1:10 curing agent to prepolymer, Sylgard 184, Dow Corning, US). It was then cured at room temperature for at least 24 h, the cured PMDS was peeled of from the silicone mold to complete the fabrication. Room temperature curing is desired in this process because it maintains high dimensional fidelity. Regular thermal curing (65° C. or higher) produces considerable size shrinkage from designed values after peeling of the PDMS structure from the master, which is not desirable for array structures because of mismatch between upper and lower chamber layouts. Inlet and outlet ports for medium perfusion chamber and for cell culture chamber were punched with sharp 23G style 2 needle. Upper and lower PDMS pieces were aligned using a microscope and quickly put into contact. Reversible bonding was achieved upon conformal contact.

Figure 20:
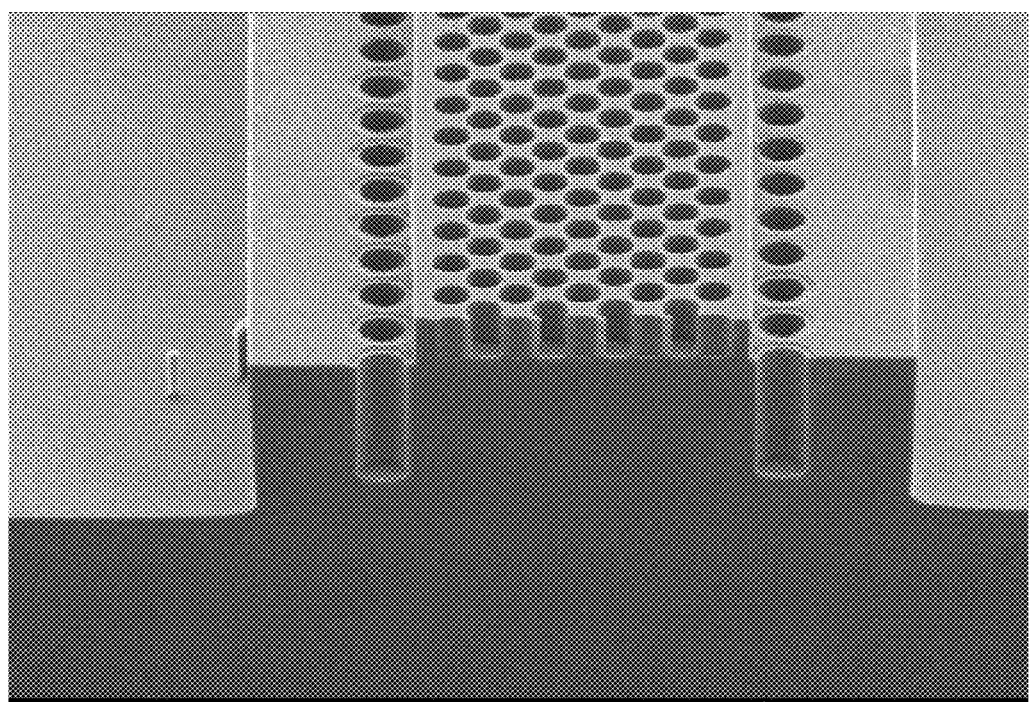
FIG. 20 is an image of a silicon master used for forming a portion of a microfluidic device.
Figure 21:
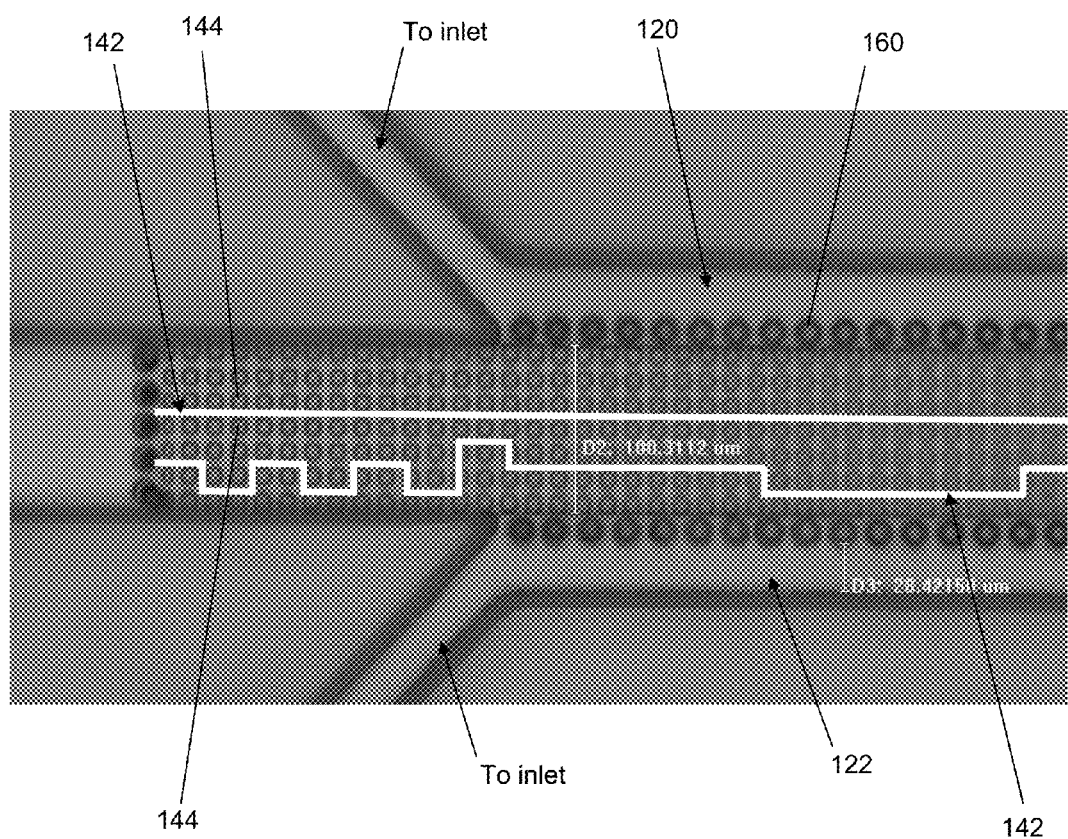
FIG. 21 is an image of a replicated assembled device.
Figure 22A:
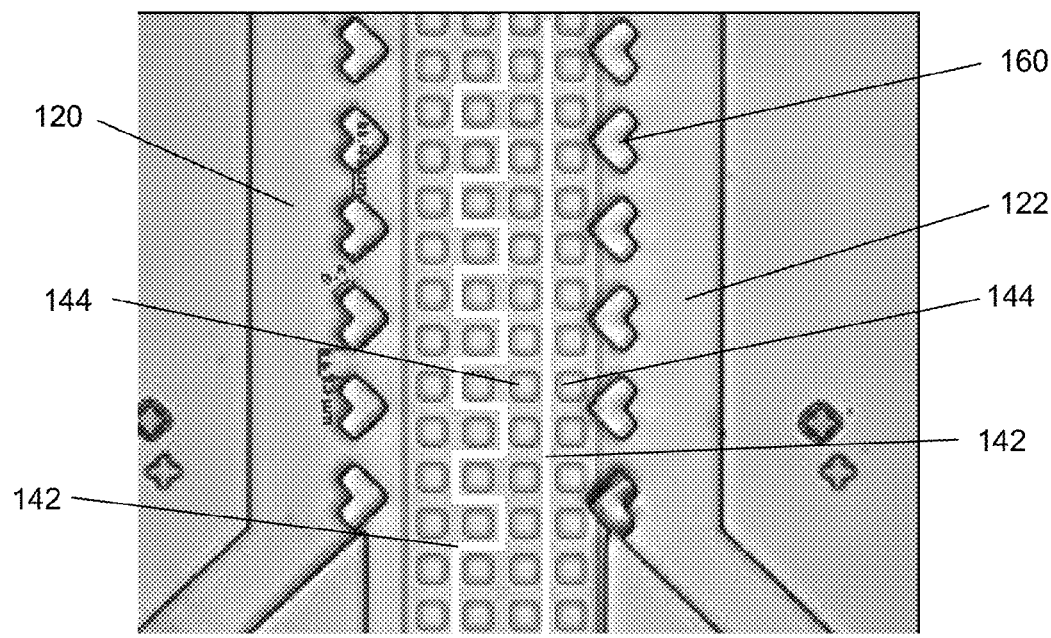
FIGS. 22A-B are images of alternative embodiments of devices, different dimensions of retention posts and bottom channel (or top channel) substructures.
Figure 22B:
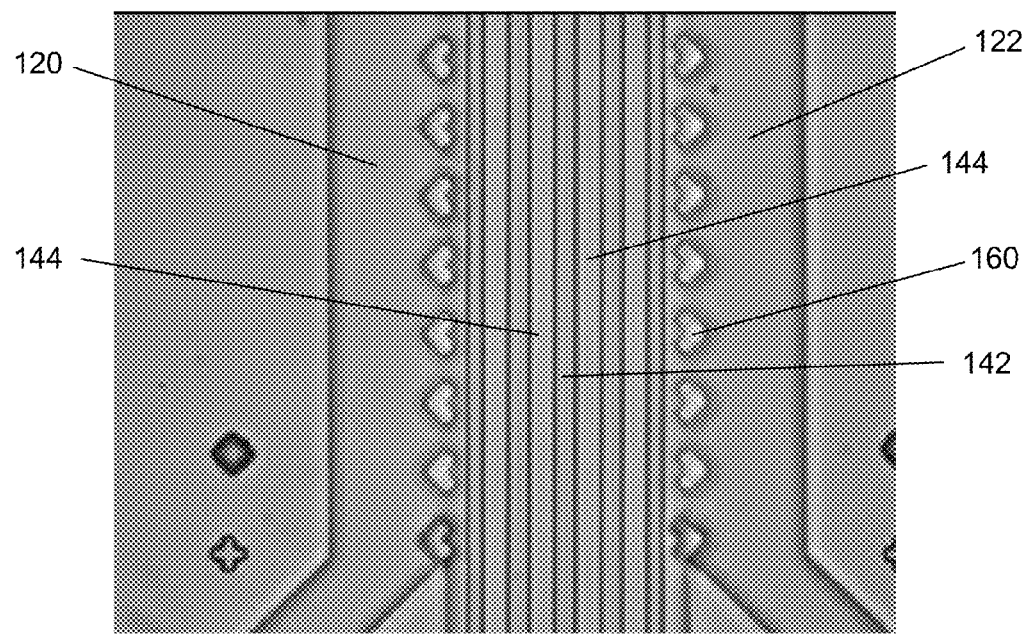

An image of an example silicone wafer mold resulting from the process described above is shown in FIG. 20. An image of a resulting replicated assembled device is shown in FIG. 21. Images of alternative embodiments of devices are shown in FIG. 22A-B, which show different dimensions of retention posts and bottom channel (or top channel) substructures. In FIGS. 21 and 22A-B, projections 144, troughs 142, retention posts 160, and perfusion channels 120, 122 are labeled for purposes of convenience. As shown in FIGS. 21, 22A and 22B, the retention posts 160, as well as the projections 144 and troughs 142, can take be of nearly any suitable shape.

In EXAMPLES 2-6 below, a microfluidic devices made as described above and having a cell chambers with a bottom structured surfaces as shown in FIGS. 14D, 22A, 22B were used. The bottom structured surface had an array of projections having a width and depth of 10 micrometers and a height of 15 micrometers. The gap distance between projections (i.e., the width of the troughs) was 10 micrometers. The height of the cell culture chamber was 45 micrometers and the length was 15,000 micrometers.

In FIG. 21 and FIG. 22A, white lines or zig-zags were added to the images to provide identification of troughs 142.

Example 2

Fluidic Characterization of the Microfluidic Device

Figure 23A:
FIGS. 23A-B are fluorescent images showing fluid flow through a microfluidic device.
Figure 23B:
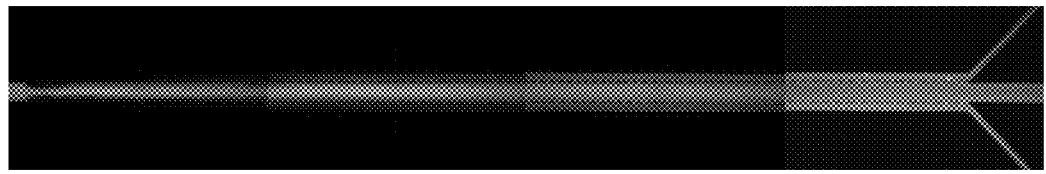

To test the mass transfer inside the device between perfusion channels and cell incubation chamber subsequent injections solutions of Sulforhodamine B ($8.9 \times 10^{-5}$ M SRB in PBS buffer) and carboxyfluoresceine ($4 \times 10^{-5}$ M in PBS buffer) dyes was performed employing a microfluidic device having a single inlet and outlet for both the left and right perfusion channels. An increase of Sulforhodamine B fluorescence intensity in the cell culture chamber was observed as a function of flow rate and time (FIG. 23A) indicating good fluidic transport across the retention barrier (posts) and between the perfusion channels and the cell chamber. Conversely, when the fluorescein ($4 \times 10^{-5}$ M in PBS buffer) was introduced via the cell chamber inlet, an increase in fluorescent intensity across the retention barrier (posts) and filling the perfusion channels was observed (FIG. 23B). In the images shown in FIGS. 23A and 23B, the left side of the image is closer to the inlet where the fluid was introduced, and the right side of the image is closer to the outlet where the fluid exited the device.

Figure 24A:
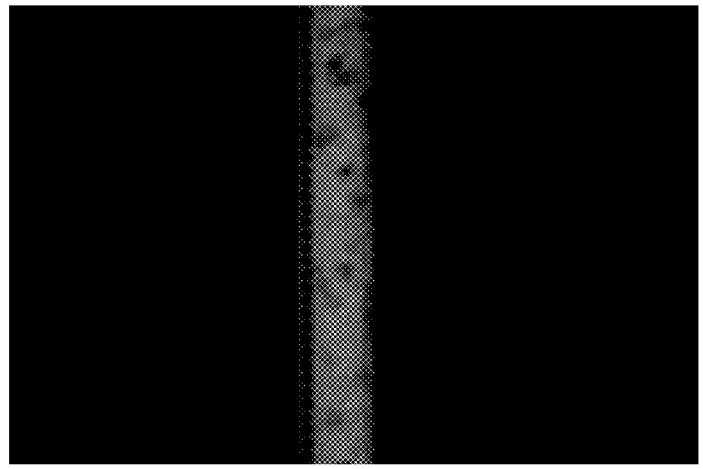
FIGS. 24A-B are fluorescent images showing fluid flow through a microfluidic device in which cells are cultured.
Figure 24B:
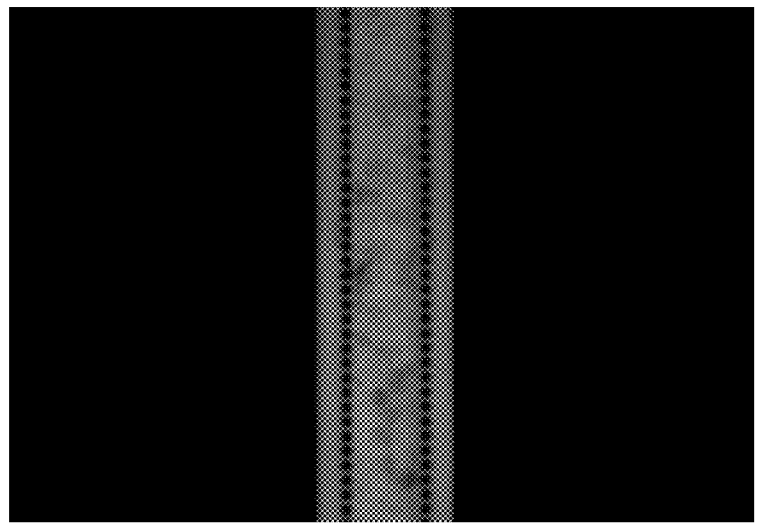

Cells were introduced into the main chamber of a microfluidic cell culture device via a cell chamber inlet. Approximately 5 microliters of suspension of primary human hepatocytes (2 million cells/ml) was used. The cells in suspension were injected into cell retention chamber at 0.5 ul/min flow rate. Injection of the cell suspension was stopped once the entire cell retention chamber was packed with the cells (approximately 10000 cells per device). Cell culture media was perfused though the device for 3 days before starting independent perfusion of bottom structure channel. Subsequent injections of non-fluorescent (cell culture media—MFE Essential Support Medium F w/MFE Culture Medium Supplement A, #K4105.X, XenoTech LLC) and fluorescent solution (dextran-rhodamine conjugate, MW 10000, 8 mg/ml in HBSS buffer) was introduced via a bottom channel inlet. As shown in FIG. 24A, affixing the cells on top of the substructures allows the introduction of independent flow through the substructures at the bottom of the cell retention chamber. This is evidenced by the flow of fluorescent dye in the region of the substructures only in FIG. 24A. The fluorescent dye did not mix or enter the left and right perfusion channels at either side of the cell chamber (compare FIG. 24A to FIG. 24B in which fluorescent die was intentionally infused in the bottom and side channels for purposes of comparison).

In the tested device, the perfusion flow rate of the substructural channel was configured to be about 10 times lower than the perfusion flow rate of the two main side perfusion channels. Accordingly, the perfusion flow in the device may be configured to effectively mimic complex extracellular fluid distribution that is observed in vivo, for example providing a gradient of bile salts as is characteristic in liver tissue.

Example 3

Long Term Cell Culture in Microfluidic Devices

Incubation of human primary hepatocytes in the microfluidic devices was performed to demonstrate the ability of supporting phenotypically active cell population for prolonged periods of time. 5,000-10,000 primary human hepatocyte cells (Cryopreserved human hepatocytes, XenoTech, Lenexa, Kans.) were plated to the microfluidic devices (via cell chamber port) and the devices were perfused with MFE cell culture medium in open-loop mode at 1 ul/min flow rate. Cell culture media was manually changed daily in 96 well plates cultures. Devices were monitored daily to track possible changes in cell morphology and health. At different time points the incubation was stopped and a live/dead stain (LIVE/DEAD viability/cytotoxicity kit for mammalian cells from Molecular Probes, Eugene, Oreg.) was performed to monitor cell survival rate and morphology. Images of cells packed in the device and the results of live/dead stain are shown in FIGS. 25-26.

Figure 25:
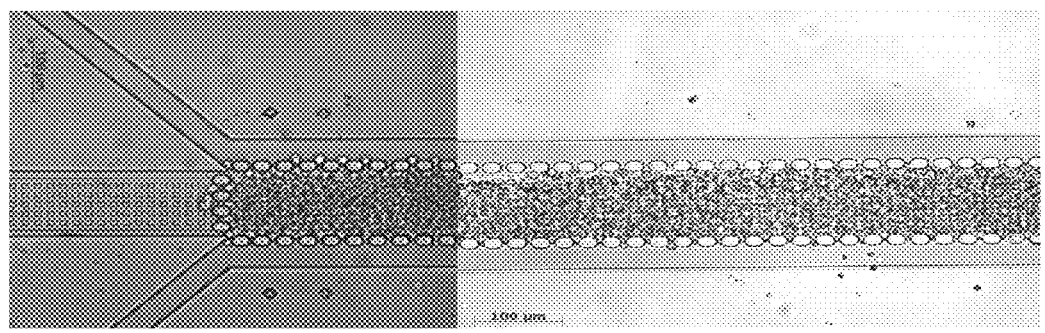
FIG. 25 is an image (20×) of human primary hepatocytes packed and cultured in a cell chamber of a microfluidic device for 7 days.
Figure 26:
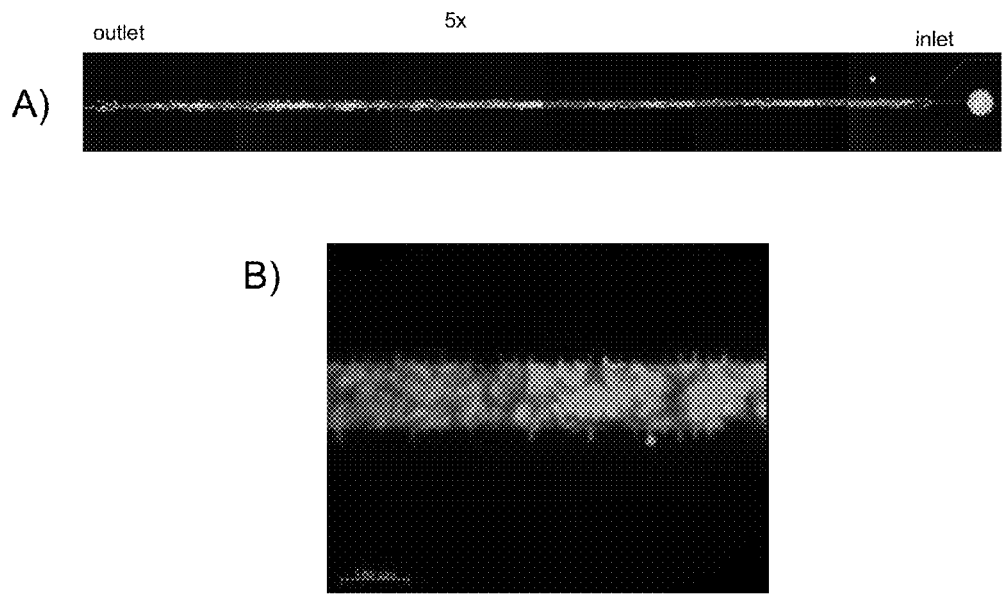
FIG. 26A-B are representative fluorescent images (A: 5×, B: 20×) showing the results of live/dead staining of hepatocytes cultured in a cell chamber of a microfluidic device after 7 days of incubation.

FIG. 25 is an image (20×) of human primary hepatocytes packed and cultured in the cell chamber of the device for 7 days. Microscopic inspection verified that the cells are packed in 3D and do not undergo spreading. The hepatocytes were observed to be retained in the cell chamber (only) and did not appear to block the perfusion channels or the perfusion across the retention barriers.

FIGS. 26A-B are representative fluorescent images (A: 5×, B: 20×) showing the results of live/dead staining after 7 days of incubation. With live/dead staining, green fluorescence indicates the cells are alive and red fluorescence indicates the cells are dead. While not apparent from the black and white reproduction presented herein, nearly 100% of the cells are alive (green fluorescence) after 7 days incubation. The images presented in FIGS. 26A-B demonstrate that microfluidic culture device is capable of providing effective perfusion of the assay reagents across the retention barrier and through the cell culture chamber that was packed with hepatocytes.

Example 4

Figure 27A:
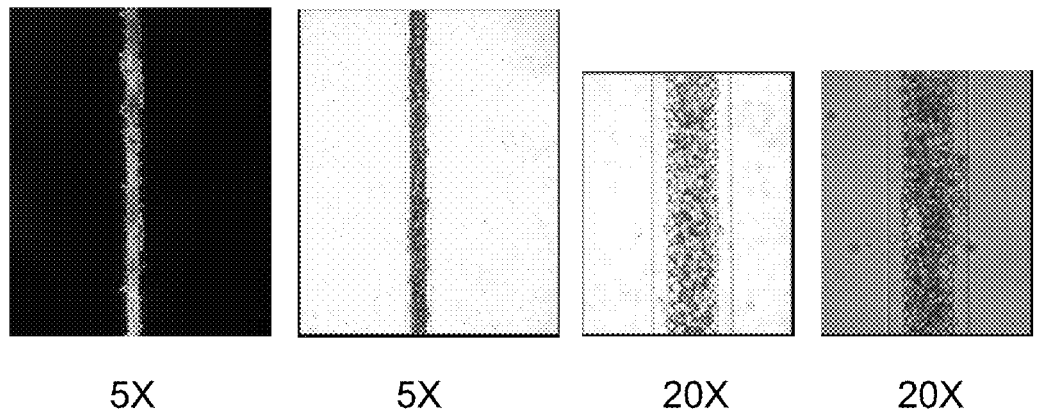
FIGS. 27A-B are fluorescent and brightfield images of hepatocytes packed in 3D in a cell chamber of a microfluidic device without bottom substructures (22A) and with bottom substructures (22B) taken after 7 days of incubation.
Figure 27B:
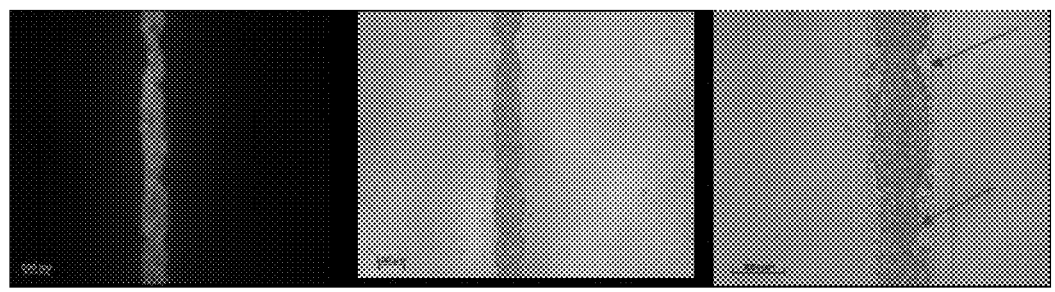

The Impact of the Substructure Feature at the Bottom of the Cell Culture Chamber FIGS. 27A-B are fluorescent and brightfield images of hepatocytes packed in 3D in the cell chamber without bottom substructures (27A) and with bottom substructures (27B) taken after 7 days of incubation. In FIG. 27A, the left most panel is a fluorescent image (5×) and the three rightmost panels are brightfield images at 5×, 20× and 20× (left to right, respectively). In FIG. 27B, the left most panel is a fluorescent image (10×), the middle panel is a brightfield image (10×), and the right panel is a brightfield image (20×).

Nearly all of the hepatocytes were alive (based on green fluorescence with live/dead staining as described above, which is not visible in the black and white reproduction provided herein), regardless of whether cultured in a device having bottom substructures or a device having no bottom substructures. However morphologic evaluation revealed that the cells cultured on the device having no bottom substructures were not tightly fused. In contrast, the hepatocytes cultured on top of the bottom substructures of the cell chamber exhibited a more tissue-like morphology with tightly fused cells (arrows in right most panel of FIG. 27B) that show smooth edges of the 3D tissue structure as evidence of how well the cells are fused, resembling a tissue-like morphology.

Example 5

The Influence of Fluidics of Cells

To test the importance of perfusion flow through perfusion channels of a microfluidic device, cells were cultured in a microfluidic device with cell culture media flow through the perfusion channels throughout and with cell culture media present in the channels under static conditions (no continuous flow). Briefly, about 10,000 cryopreserved human hepatocytes (XenoTech, Lenexa, Kans.) were introduced into a device. A perfusion flow rate of 5 uL/h was used. For static conditions, cell culture media was changed manually daily. Cells were incubated for a total of 7 days.

Figure 28:
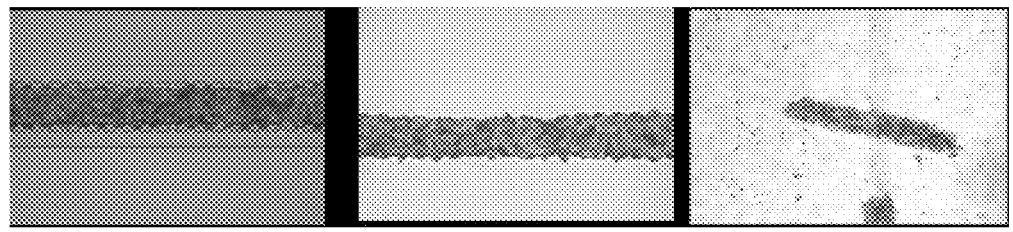
FIG. 28 shows three brightfield images of cells cultured in a microfluidic device under perfusion conditions. In the left panel, cells are shown in an assembled device. In the middle panel, cells are shown after the device cover was removed. In the right panel, cells are shown after being dislodged from the device.

FIG. 28 shows three brightfield images of cells cultured under perfusion conditions. In the left panel, cells are shown in an assembled device. In the middle panel, cells are shown after the device cover was removed. The cells appear to be fused and maintained their configuration following removal of the cover. In the right panel, cells are shown after being dislodged from the device. Again, the cells maintained their fused configuration.

Figure 29:
FIG. 29 shows three brightfield images of cells cultured under static conditions. In the left panel, cells are shown in an assembled device. In the middle panel, cells are shown after the device cover was removed. In the right panel, cells are shown after being dislodged from the device.

FIG. 29 shows three brightfield images of cells cultured under static conditions. In the left panel, cells are shown in an assembled device. In the middle panel, cells are shown after the device cover was removed. The cells appeared dead, individual and did not form a fused-tissue like structure. In the right panel, cells are shown after being dislodged from the device. Again, the cells appeared dead, individual and did not form a fused-tissue like structure.

Figure 30:
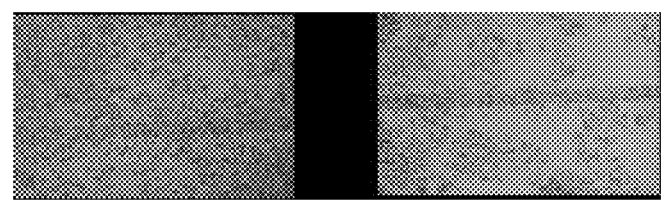
FIG. 30 shows two brightfield images of cells cultured on a 96 well plate having the structured bottom surface of the microfluidic device replicated on the bottom surface of the well. The image on the left is of cells cultured on plasma treated PDMS substrate. The image on the right is on cells cultured on non-treated PDMS.

FIG. 30 shows two brightfield images of cells cultured on a 96 well plate having the structured bottom surface of the microfluidic device replicated on the bottom surface of the well. About 60,000 cryopreserved human hepatocytes (XenoTech LLC, Lenexa, Kans.) were seeded per well in MFE Essential Plating Medium F (#K4000). After 24 h incubation, the medium was changed to MFE Essential Support Medium F w/MFE Culture Medium Supplement A (#K4105.X, XenoTech LLC). During the incubation medium was changed daily. The cells were incubated for 7 days. The image on the left is of cells cultured on plasma treated PDMS substrate. The image on the right is on cells cultured on non-treated PDMS. In both cases, the static cell culture conditions did not support a 3D tissue-like cellular structure. Hepatocytes cultured on structured PDMS surface in 96 well plate under static conditions formed a monolayer culture and did not preferentially recognize structured regions relative to flat regions.

The microfluidic device provides multiple independent perfusion channels for cells culture in continuous media (fluid) flow. Fluid perfusion based on the design dimensions mimics the hepatic circulation providing efficient continuous transport of gas and nutrients to the hepatocytes and removal of metabolites or cellular waste. The microstructured lower flow channel at the bottom of the cell chamber allow for independent perfusion from the other two perfusion channels of the device. The multiple perfusion channels effectively transport media (nutrients), assay reagents and cellular waste, thereby, maintaining a viable cell culture for an extended period of time. Also, the dynamic cell culture conditions influence the formation of 3D cells that are tightly fused into a tissue-like cellular structure without the addition of animal derived or synthetic matrices or coagulants that remains intact when dislodged from the device (FIG. 28).

Static culture conditions in the device resulted in individual cells that died during incubation and readily dispersed when the device was dissembled (FIG. 29). Likewise, static cell culture conditions with a structured PDMS surface in 96 well plate, a replication of the bottom of the cell chamber of the device, did not support a 3D tissue-like cellular structure. Hepatocytes cultured on structured PDMS surface in 96 well plate under static conditions formed a monolayer culture and did not preferentially recognize structured regions relative to flat regions (FIG. 30).

Example 6

Restoration of Membrane Polarity and Hepatocyte Specific Function

Hepatocytes, in vivo, are supported in three dimensional conformation by a combination of extra cellular matrix (ECM) and other non-parenchymal cells. In conventional in vitro 2D cell culture format primary hepatocytes dedifferentiate rapidly because of limited cell-cell interaction and the inability to restore in vivo-like cellular organization. The maintenance of differentiated functions of primary hepatocytes is dependent on the restoration of morphological structure and membrane polarity. The metabolic functions of primary hepatocytes have been clearly correlated to the polarity of hepatocytes induced by different culture configurations. Therefore, restoration of hepatocyte polarity is important in the maintenance of hepatocyte function.

Figure 31:
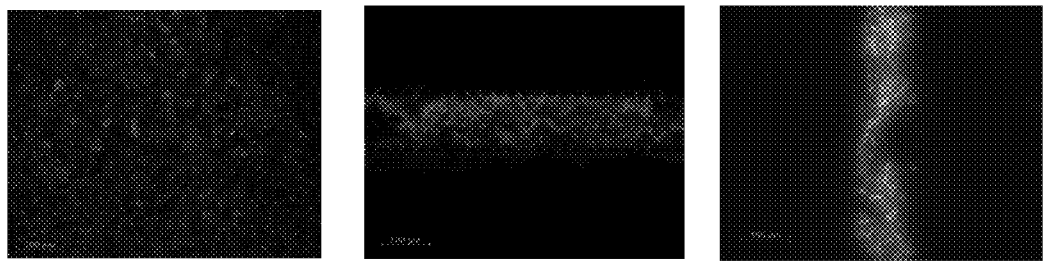
FIG. 31 shows fluorescent images of MRP2 protein immunostained human primary hepatocytes cultured in a conventional 96 well plate (left panel), and in a microfluidic device (middle and right panels).
Figure 32:
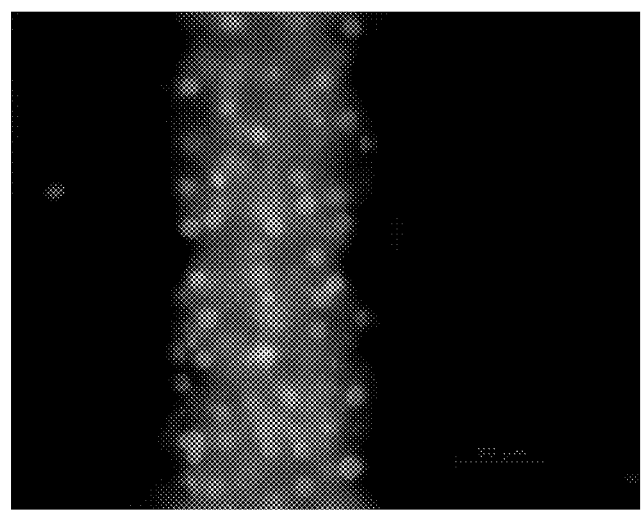
FIG. 32 is a fluorescent image of connexin-32 protein immunostained human primary hepatocytes cultured in a microfluidic device.

As mentioned above, the substructures at the bottom of the cell chamber provide a lower flow channel through these microstructures which provides independent perfusion. This design feature influences the formation of tightly fused, tissue-like cellular structures. The 3D cell culture morphology promotes the restoration of cell membrane polarity (FIGS. 31-32), and the restoration of hepatocyte specific function, such as transport function (FIG. 33) without the addition of animal derived or synthetic matrices or coagulants. Cell membrane polarity is evidenced by the extended formation of bile canaliculi structures in 3D shown by the expression of the bile canalicular marker, MRP2, and gap junction protein, Connexin 32, via immunostaining in FIGS. 31-32. Briefly, after seven day perfusion culture inside microfluidic device, cells were fixed with 3% paraformaldehyde in PBS, permeabilized with Triton X-100 (1% in PBS) and incubated with a mixture of primary antibodies (1:100 dilution by blocking buffer, mouse anti-Connexin 32 unconjugated monoclonal antibody, 25 ug/ml; Rabbit anti-MRP2, polyclonal antibody, 9 ug/ml, Abcam) overnight at 4° C. After the incubation, the sample was washed with 0.1% Tween 20 in PBS and incubated with secondary antibodies conjugated to FITC (494/518 nm) and Cy3 (550/570 nm) fluorescent labels. Unbound antibodies were washed out with washing buffer (3×200 uL) and the sample was covered with 20 uL of Vectashield mounting solution supplemented with fluorescent DAPI stain to stain the cells' nuclei.

Figure 33A:
FIGS. 33A-B are images of a fluorescine diacetate transport function assay for MRP2 hepatocyte transporter of cells cultured in a conventional 96 well plate (A) and in a microfluidic device (B).

In conventional 2D cell culture the expression of MRP2 protein when present is observed as tiny unconnected dots between some cells illustrating the limited formation of bile canaliculi structures (see FIG. 33A, in which hepatocytes were cultured on a conventional 96 well plate). After 7-day culture on conventional 96 well plate, cells were incubated for 10 min with MPR2 substrate (5 µM 5-(6) carboxy-2'7' dichlorofluorescein diacetate solution in cell culture media). Carboxy-2'7' dichlorofluorescein diacetate was absorbed by the cell and metabolized. The metabolites are actively excreted by MRP2 protein into bile canalicular structures. Transposition of fluorescein metabolites was monitored by fluorescent microscopy (494/518 nm), thus, dynamic functional stain of bile canalicular structures inside the cell aggregates was obtained.

Figure 33B:
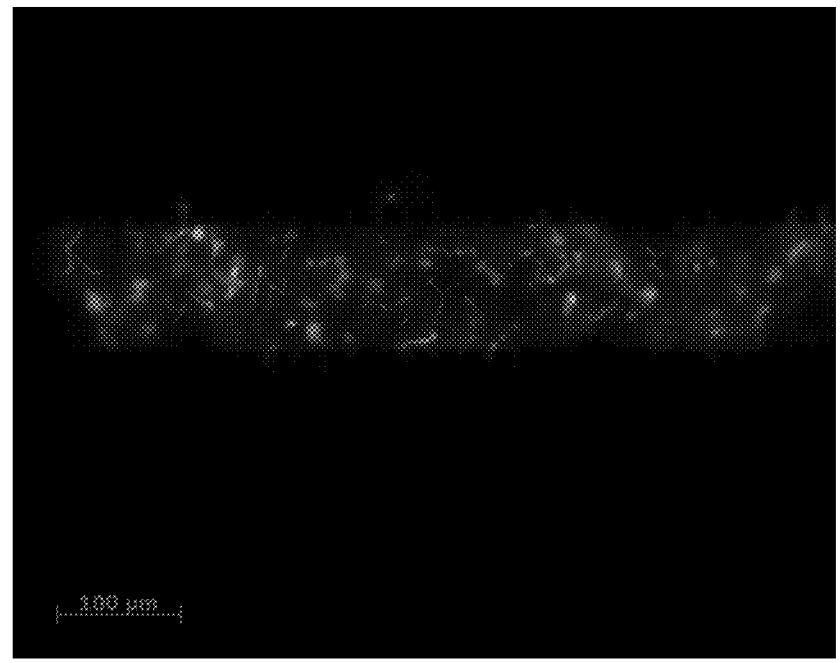

The MRP2 protein is also responsible for transport function from the cells into the bile canaliculi structure. Transport function, in recent years, is often referred to as Phase III of drug metabolism in the liver and is critical for removal of drug metabolites or the active transport of drug compounds into cells. FIG. 33B presents one image of the dynamic assay where fluorescein diacetate was passively absorbed by the hepatocytes and actively transported via MRP2 transporter protein into extended bile canaliculi structures demonstrating hepatocyte specific function in the microfluidic device. Briefly, MPR2 substrate (5 µM 5-(6) carboxy-2'7' dichlorofluorescein diacetate solution in cell culture media) was perfused though the device for 10 min at 1 uL/min flow rate. Transposition of fluorescein metabolites can be monitored by fluorescent microscopy (494/518 nm), thus, dynamic functional stain of bile canalicular structures inside the device was can be obtained. This function is largely driven by restoration of polarity via cell-cell signaling and the formation of tightly fused, tissue-like, 3D cellular structure. To our knowledge, the formation of such extended bile canaliculi structure in 3D (restoration of membrane polarity) and the demonstration of transport function of human primary hepatocytes in a microfluidic device has not be shown or reported before.

In summary, the present disclosure describes a microfluidic device design and methods for functional maintenance of cells in highly differentiated state in vitro. The ability of cells to support its in vivo functions while being cultured in vitro system have high importance in tissue engineering applications and evaluating therapeutic candidates. The described cell culture systems may be used to support long term cell cultures, to promote restoration of in vivo like cellular organization that increase phenotype specific activity of cultured cells thus providing physiologically relevant information for cell-based assays.

Thus, embodiments of MICROFLUIDIC DEVICE FOR CELL CULTURE are disclosed. One skilled in the art will appreciate that the cell culture apparatuses and methods described herein can be practiced with embodiments other than those disclosed. The disclosed embodiments are presented for purposes of illustration and not limitation.

What is claimed is:
1. A cell culture apparatus comprising:
    a cell retention chamber having a first structured surface, wherein the structured surface includes a major surface from which a plurality of projections extend into the chamber, wherein the plurality of projections are arranged to suspend cells cultured in the chamber above the major surface; and
    a first perfusion channel (i) configured to carry a cell culture medium and (ii) forming a plurality of openings in communication with the cell retention chamber, the openings configured to prevent cells from the retention chamber from entering the perfusion channel.
2. A cell culture apparatus according to claim 1, wherein each of the plurality of projections has a cell contact surface configured to contact one or more of the cells, wherein the cell contact surface has a diametric dimension less than 15 micrometers.

3. A cell culture apparatus according to claim 2, wherein the cell contacting surface of each of the projections has a diametric dimension of between 5 micrometers and 10 micrometers.

4. A cell culture apparatus according to claim 1, wherein each of the projections extend from the major surface to a height of between 5 micrometers to 25 micrometers.

5. A cell culture apparatus according to claim 1, wherein the distance between neighboring projections is less than 15 micrometers.

6. A cell culture apparatus according to claim 1, wherein the distance between neighboring projections is between 5 micrometers and 10 micrometers.

7. A cell culture apparatus according to claim 1, wherein a trough is formed between the plurality of projections, wherein the trough extends the length of the structured surface.

8. A cell culture apparatus according to claim 7, wherein the apparatus further comprises an inlet in fluid communication with the trough.

9. A cell culture apparatus according to claim 8, wherein the apparatus further comprises an outlet in fluid communication with the trough, and wherein the outlet is the same or different from the inlet.

10. A cell culture apparatus according to any of the preceding claims, further comprising a second perfusion channel forming a plurality of openings in communication with the cell retention chamber, the openings being of a dimension configured to prevent cells from the culture chamber from entering the second perfusion channel.

11. A cell culture apparatus according to claim 10, wherein the first and second perfusion channels are on generally opposing sides of the cell retention chamber.

12. A cell culture apparatus according to claim 10, wherein the cell retention chamber has a width of between 80 micrometers and 110 micrometers.

13. A cell culture apparatus according to claim 10, wherein the cell retention chamber has a height of between 40 micrometers and 50 micrometers.

14. A cell culture apparatus according to claim 10, wherein the first perfusion channel has a height of between 30 micrometers and 50 micrometers and has a width of between 30 micrometers to 50 micrometers.

15. A cell culture apparatus comprising:
a cell retention chamber having a first structured surface, wherein the structured surface includes a major surface from which a plurality of projections extend into the chamber, wherein each of the plurality of projections has a cell contact surface opposing the major surface, wherein the cell contact surface has a diametric dimension of less than 15 micrometers, each of the projections extend from the major surface to a height of greater than 5 micrometers, and wherein the distance between neighboring projections is less than 15 micrometers, wherein the structured surface includes a trough, at least a portion of which is formed between neighboring projections, wherein the trough extends the length of the structured surface;
a trough inlet in fluid communication with the trough;
a chamber inlet in fluid communication with the cell retention chamber; and
a first perfusion channel (i) configured to carry a cell culture medium and (ii) forming a plurality of openings in communication with the cell retention chamber, the openings configured to prevent cells from the retention chamber from entering the perfusion channel.

16. A cell culture apparatus according to claim 15, wherein the trough is configured to be at least partially isolated from the chamber when cells are cultured in the chamber.

17. A cell culture apparatus according to claim 2, wherein each of the projections extend from the major surface to a height of between 5 micrometers to 25 micrometers.

18. A cell culture apparatus according to claim 2, wherein the distance between neighboring projections is less than 15 micrometers.

19. A cell culture apparatus according to claim 2, wherein the distance between neighboring projections is between 5 micrometers and 10 micrometers.

20. A cell culture apparatus according to claim 2, wherein a trough is formed between the plurality of projections, wherein the trough extends the length of the structured surface.

* * * * *